United States Patent
Leblond et al.

(10) Patent No.: US 9,399,628 B2
(45) Date of Patent: Jul. 26, 2016

(54) 1-ARYL-1-HYDROXY-2,3-DIAMINO-PROPYL AMINES, 1-HETEROARYL-1-HYDROXY-2,3-DIAMINO-PROPYL AMINES AND RELATED COMPOUNDS HAVING ANALGESIC AND/OR IMMUNO STIMULANT ACTIVITY

(71) Applicant: Allergan, Inc., Irvine, CA (US)

(72) Inventors: Bertrand Leblond, Paris (FR); Eric Beusoleil, Paris (FR); Thierry Taverne, St. Martin Boulogne sur Mer (FR); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/949,468

(22) Filed: Jul. 24, 2013

(65) Prior Publication Data

US 2013/0310383 A1 Nov. 21, 2013

Related U.S. Application Data

(60) Division of application No. 13/196,132, filed on Aug. 2, 2011, now Pat. No. 8,513,288, and a continuation of application No. 11/814,601, filed as application No. PCT/US2006/002570 on Jan. 25, 2006, now Pat. No. 8,013,000.

(60) Provisional application No. 60/647,271, filed on Jan. 26, 2005.

(51) Int. Cl.
| | |
|---|---|
| *A61K 31/5375* | (2006.01) |
| *C07D 265/30* | (2006.01) |
| *A61K 31/40* | (2006.01) |
| *A61K 31/4025* | (2006.01) |
| *C07D 213/64* | (2006.01) |
| *C07D 295/12* | (2006.01) |
| *C07D 319/18* | (2006.01) |
| *A61K 31/4409* | (2006.01) |
| *A61K 31/4439* | (2006.01) |
| *A61K 31/4545* | (2006.01) |
| *A61K 31/4709* | (2006.01) |
| *A61K 31/496* | (2006.01) |
| *A61K 31/5377* | (2006.01) |
| *A61K 31/541* | (2006.01) |

(52) U.S. Cl.
CPC .............. *C07D 265/30* (2013.01); *A61K 31/40* (2013.01); *A61K 31/4025* (2013.01); *A61K 31/4409* (2013.01); *A61K 31/4439* (2013.01); *A61K 31/4545* (2013.01); *A61K 31/4709* (2013.01); *A61K 31/496* (2013.01); *A61K 31/5375* (2013.01); *A61K 31/5377* (2013.01); *A61K 31/541* (2013.01); *C07D 213/64* (2013.01); *C07D 295/12* (2013.01); *C07D 319/18* (2013.01)

(58) Field of Classification Search
CPC .......................... A61K 31/5375; C07D 265/30
USPC ......................................... 514/239.5; 544/162
See application file for complete search history.

(56) References Cited

U.S. PATENT DOCUMENTS

| | | | | |
|---|---|---|---|---|
| 2,514,380 | A | * | 7/1950 | Duschinsky .................. 564/369 |
| 5,767,121 | A | | 6/1998 | Takatani et al. |
| 5,907,039 | A | * | 5/1999 | Jinbo et al. .................... 540/609 |
| 5,916,911 | A | | 6/1999 | Shayman et al. |
| 5,945,442 | A | | 8/1999 | Shayman et al. |
| 5,952,370 | A | | 9/1999 | Shayman et al. |
| 5,976,781 | A | | 11/1999 | Haldar et al. |
| 6,030,995 | A | | 2/2000 | Shayman et al. |
| 6,051,598 | A | | 4/2000 | Shayman et al. |
| 6,407,064 | B2 | | 6/2002 | Masuda et al. |
| 8,013,000 | B2 | | 9/2011 | Leblond et al. |
| 2002/0198240 | A1 | | 12/2002 | Shayman et al. |
| 2003/0050299 | A1 | | 3/2003 | Hirth et al. |
| 2003/0153768 | A1 | | 8/2003 | Hirth |

FOREIGN PATENT DOCUMENTS

| | | |
|---|---|---|
| EP | 0720852 | 7/1996 |
| EP | 0765865 | 4/1997 |
| EP | 0782992 | 7/1997 |
| JP | 09-216858 | 8/1997 |
| JP | 10-345671 | 12/1998 |
| JP | 10-324671 | * 12/2008 |
| WO | 95-05177 | 2/1995 |
| WO | 01-04108 | 1/2001 |
| WO | 01-38228 | 5/2001 |

(Continued)

OTHER PUBLICATIONS

Abe, Akira et al, Improved Inhibitors of Glucosylceramide Synthase, J. Biochem., 1992, 191-196, 111.

Abe, Akira et al, Structural and Stereochemical Studies of Potent Inhibitors of Glucosylceramide Synthase and Tumor Cell Growth, Journal of Lipid Research, 1995, 611-621, 36.

Bixler, Robert et al, Synthesis of β-(4-Pyridyl)-DL-Alanine and of β-(4-Pyridyl-l-oxide)-DL-, D-, and L-Alanine, Journal of Organic Chemistry, Apr. 1958, 575-584, 23, California Institute of Technology.

Burford, Hugh et al, Pharmacological Studies on Some New Acrylic Acid Amide Derivatives, Journal of Pharmaceutical Sciences, Dec. 1965, 1750-1754, 54(12).

(Continued)

Primary Examiner — Rebecca Anderson
(74) Attorney, Agent, or Firm — Jonathan Bass

(57) ABSTRACT

Compounds of the formula

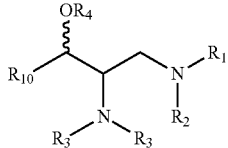

Formula 2 where the variables have the meaning defined in the specification have analgesic and/or immunostimulant effect in mammals.

8 Claims, No Drawings

(56) References Cited

FOREIGN PATENT DOCUMENTS

| WO | 01-47874 | 7/2001 |
|----|----------|--------|
| WO | 02-12185 | 2/2002 |
| WO | 02-062777 | 8/2002 |
| WO | 03-008399 | 1/2003 |
| WO | 03-045928 | 6/2003 |
| WO | 2005-063275 | 7/2005 |

OTHER PUBLICATIONS

Dixon, W. J., Efficient Analysis of Experimental Observations, Ann. Rev. Pharmacol Toxicol, 1980, 441-462, 20, Annual Reviews Inc.

Gregory, H. et al., Polypeptides. Part VII. Variations of the Phenylalanyl Position in the C-Terminal Tetrapeptide Amide Sequence of the Gastrins, Journal of the Chemical Society, 1968, 531-540.

Husain, Arifa et al, syn-Selective Additions to Garner Aldehyde: Synthesis of a Potent Glucosylceramide Synathase Inhibitor, Tetrahedron Letters, 2002, 8621-8623, 43.

Inokuchi et al, Amino Alcohol esters as ceramide analogs and pharmaceuticals containing them for treatment of nerve diseases, 1998, 1 pg.

Inokuchi, Jin-Ichi et al, A Synthetic Ceramide Analog (L-PDMP) Up-regulates Neuronal Function, Annals New York Academy of Sciences, 1998, 219-224, 1.

Inokuchi, Jin-Ichi et al, Antitumor Activity Via Inhibition of Glycosphingolipid Biosynthesis, Cancer Letters, 1987, 23-30, 38.

Inokuchi, Jin-Ichi et al, Preparation of the active isomer of 1-phenyl-2-decanoylamino-3-morpholino-1-propanol, inhibitor of murine glucocerebrosideb synthetase, J. Lipid Res., 1987, 565-571, 28.

Jimbo, Masayuki et al, Development of a New Inhibitor of Glucosylceramide Synthase, J. Biochem., 2000, 485-491, 124.

Kastron et al., Latvijas PSR Zinatnu Akademijas Vestis, Kimijas Serija, 1965, 474-477, 4.

Kim, Sun Ho et al., An experimental model for peripheral neuropathy produced by segmental spinal nerve ligation in the rat, Pain, 1992, 355-363, 50.

Kurosawa, Motohiro et al, 14C-Labeling of a Novel Atypical β-Adrenoceptor Agonist, SM-11044, Journal of Labelled Compounds and Radiopharmaceuticals, 1996, 285-297, 38 (3).

Lee, Lihusueh et al., Improved Inhibitors of Glucosylceramide Synthase, The Journal of Biological Chemistry, 1999, 14662-14669, vol. 274, No. 21, The American Sopciety for Biochemistry & Molecular Biology, Inc.

Mitchell, Scott et al, Glycosyltranferase Inhibitors: Synthesis of D-threo-PDMP, L-threo-PDMP, and Other Brian Glucosylceramide Synthase Inhibitors From D- or L-Serine, J. Org. Chem., 1998, 8837-8842, 53.

Miura, Tsuyoshi et al, Synthesis and Evaluation of morpholino- and Pyrrolidinosphingolipids as Inhibitors of Glucosylceramide Synthase, Bioorganic & Medicinal Chemistry, 1998, 1481-1489, 6.

Mizutani, Akihiro et al, Effects of Glucosylceramide Synthase Inhibitor and Ganglioside GQ1b on Synchronus Oscillations of Intracellular Ca2+ in Cultured Cortical Neurons, Biochemical and Biophysical Research Communications, 1996, 494-498, 222.

Nishida, Atsushi et al, Practical Synthesis of Threo-(1S, 2S)- and Erythro-(1R, 2S)-1-Phenyl-2-Palmitoylamino-3-morpholino-1-propanol (PPMP) From L-Serine, Synlett, Apr. 1998, 389-390.

Radin, Norman et al, Use of an Inhibitor of Glucosylceramide Synthesis, D-1-Phenyl-2-decanoylamino-3-morpholino-1-propanol, Neuroprotocols: A Companion to Methods in Neurosciences, 1993, 145-155, 3.

Shin, Seong-Ho et al, Stereoselective Synthesis of Enantiomerically Pure D-Threo-PDMP; Manipulation of Core 2,3-Diamino alchohol Unit, Tetrahedron: Asymmetry, 2000, 3293-3301, 11.

Slavish, Jacob et al, New PDMP Analogues Inhibit Process Outgrowth in an Insect Cell Line, Bioorganic & Medicinal Chemistry, 2004, 1487-1490, 14.

Tabanella, Stefania et al., Preparation of Enantiomerically Pure Pyridyl Amino Acids from Serine, Organic & Biomolecular Chemistry, 2003, 4254-4261, 1 (23).

Theeraladanon, Chumpol et al, A Novel Synthesis of Substituted Quinolines Using Ring-Closing Metathesis (RCM): Its Application to the Synthesis of Key Intermediates for Anti-Malarial Agents, Tetrahedron, 2004, 3017-3035, 60.

Tucker, Thomas et al., A Series of Potent HIV-1 Protease Inhibitors Containing a Hydroxyethyl Secondary Amine Transition State Isostere: Synthesis; Enzyme Inhibition, and Antiviral Activity, Journal of Medicinal Chemistry, 1992, 2525-2533, 35 (14).

Venturella, Vincent et al, Synthesis of Several Derivatives of Phenyl(2-hdroxy-3-yrazyl)carbinol, Journal of Pharmaceutical Sciences, Feb. 1963, 142-146, 52(2).

Vlasenko et al, Study of the Anesthetic Properties of Beta Amino Alcohols, Biologicheskii Zhurnal Armenii, 1975, 18-20, 28(11).

Vunnam, Ranga Rao et al, Analogs of Ceramide That Inhibit Glucocerebroside Synthetase in Mouse Brain, Chemistry and Physics of Lipids, 1980, 265-278, 26.

* cited by examiner

1-ARYL-1-HYDROXY-2,3-DIAMINO-PROPYL AMINES, 1-HETEROARYL-1-HYDROXY-2,3-DIAMINO-PROPYL AMINES AND RELATED COMPOUNDS HAVING ANALGESIC AND/OR IMMUNO STIMULANT ACTIVITY

CROSS-REFERENCE TO RELATED APPLICATION

This application is a divisional application of Ser. No. 13/196,132, filed Aug. 2, 2011, which is a continuation of Ser. No. 11/814,601, filed Mar. 17, 2008, which is a §371 National Stage of PCT/US2006/002570, filed Jan. 25, 2006, which claims the benefit of U.S. Provisional Application Ser. No. 60/647,271, filed Jan. 26, 2005, each of which is hereby incorporated by reference herein.

FIELD OF THE INVENTION

The present invention relates to derivatives of 1-aryl-1-hydroxy-2,3-diamino-propyl amines, 1-heteroaryl-1-hydroxy-2,3-diamino-propyl amines and to related compounds having analgesic and in some cases immunostimulant activity.

The present invention also relates to pharmaceutical compositions containing these compounds as active ingredient for alleviating or eliminating pain in mammals and/or stimulating the immune system in mammals and to methods of using said pharmaceutical compositions as analgesics and/or immunostimulants.

BACKGROUND ART

1-Phenyl-2-decanoylamino-3-morpholino-1-propanol (PDMP) was discovered by Vunam, R. R. and Radin, N., *Chem. Phys. Lipids*, 26, 265-278, 1980. Preparation of PDMP is described in Inokuchi, J. et al., *J. Lipid Res.* 28, 565-571, 1987; Radin, A. et al., *NeuroProtocols*, 3(2), 145-55, 1993; Radin, A. et al., *J. Lipid Res.* 36, 611-621, 1995 and U.S. Pat. No. 5,916,911.

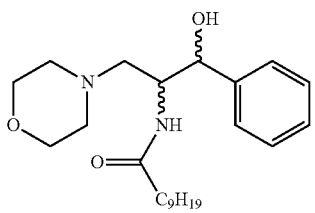

PDMP
mixture of DL-erythro and
DL-threo isomers

These derivatives inhibit glucosylcer//amide (GlcCer) formation by inhibiting the enzyme GlcCer synthase, thereby lowering the level of glycosphingolipids.) The isomers most active have the R,R-(D-threo)-configuration. Four enantiomers are produced during the synthesis. Because only the D-threo enantiomers are active in inhibiting the glucosylceramide synthase, resolution of the active D-threo inhibitors was performed by chiral chromatography.

Moreover, D-threo-PDMP has antitumor activity via inhibition of glycosphingolipid biosynthesis as described by Inokuchi J., *Cancer Letters* 38(1-2), 23-30, 1987.

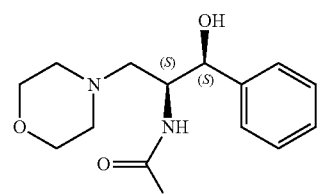

L-threo-PDMP

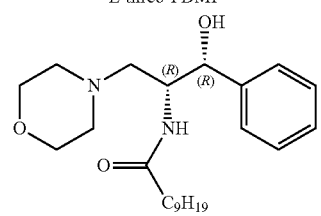

D-threo-PDMP

Furthermore, it was also reported that D-threo-PDMP suppresses synaptic function by Mizutani A. et al., Biochem. Biophys. Res. Commun., 222, 494-498, 1996.

Preparation of enantiomerically pure D-threo-PDMP has been reported by Mitchell, Scott A. [*J. Org. Chem.*, 63 (24), 8837-8842, 1998]; Miura, T. et al, [Bioorg. Med. Chem., 6, 1481-1498, 1998]; Shin, S. et al., [*Tetrahedron asymmetry*, 11, 3293-3301, 2000]; WO 2002012185.

L-threo-PDMP is an agent for treating neuronal diseases WO 95/05177. This compound is also described to be an agent for protecting brain in U.S. Pat. No. 6,407,064. Moreover treatment with L-threo-PDMP after transient forebrain ischemia in rats ameliorated the deficit of a well learned spatial memory by an 8-arm maze task, suggesting a potential for neurodegenerative disorders as described by Inokuchi et al., *Ann. N.Y. Acad. Sci.*, 845(1), 219-224, 1998 and JP 10324671 (Seikagaku Kogyo Co.).

A stereoselective synthesis of enantiomerically pure D-threo-PDMP has also been described by Shin, S. et al., *Tetrahedron asymmetry*, 11, 3293-3301, 2000 and WO 2002012185 the key step is the regioselective cleavage by nitrogen nucleophiles, as morpholine, of the C(3)-N-bond of non-activated enantiomerically pure aziridine-2-methanols.

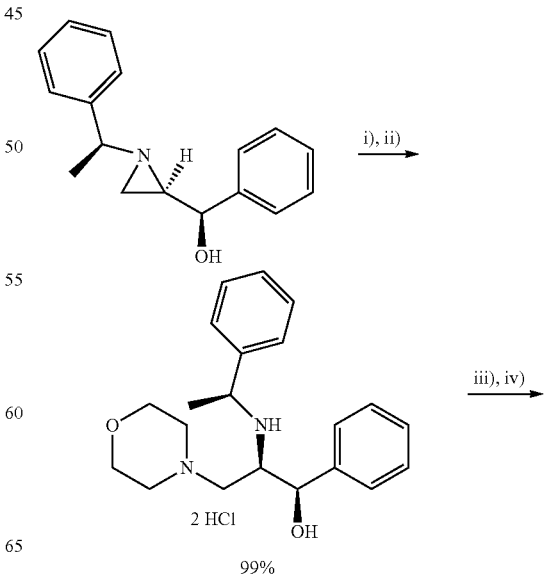

-continued

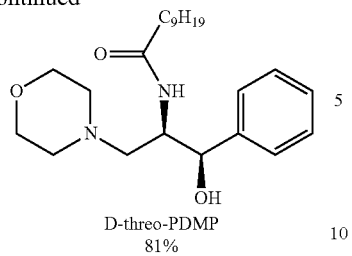

D-threo-PDMP
81% i) TMS—I, CH₃CN ii) a) morpholine b) HCl iii) Pd(OH)₂, H₂, AcOH, MeOH, 40° C. iv) 10% NaOH, decanoyl chloride 81%

On the other hand, the synthesis of enantiomerically pure (1S,2S)-1-phenyl-2-decanoylamino-3-morpholino-1-propanol (L-threo-PDMP) from L-serine has also been described by Mitchell, Scott A., *J. Org. Chem.*, 63 (24), 8837-8842, 1998.

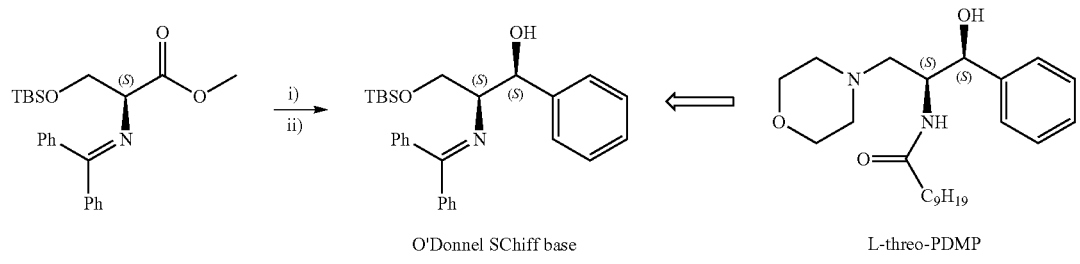

O'Donnel SChiff base i) iBU₅Al₂H ii) PhMgBr

Other known methods to obtain L-threo-PDMP are described by Miura, T. et al, *Bioorg. Med. Chem.*, 6, 1481-1498, 1998 and in JP-A-9-216858. L-threo-PDMP is an agent for treating neuronal diseases WO 95/05177. This compound is also described to be an agent for protecting brain in U.S. Pat. No. 6,407,064. Moreover treatment with L-threo-PDMP after transient forebrain ischemia in rats ameliorated the deficit of a well learned spatial memory by an 8-arm maze task, suggesting a potential for neurodegenerative disorders as described by Inokuchi et al., *Ann. N.Y. Acad. Sci.*, 845(1), 219-224, 1998 and JP 10324671 (Seikagaku Kogyo Co.).

Synthesis of (1S,2S)-threo- and (1R,2S)-erythro-1-phenyl-2-palmitoylamino-3-N-morpholino-1-propanol (PPMP) were described starting from Garner aldehyde of L-serine, by Nishida, A., *Synlett*, 4, 389-390, 1998.

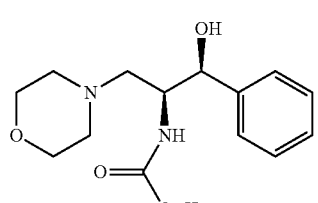

L-threo-PPMP

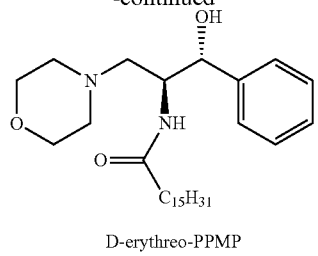

D-erythreo-PPMP

Compounds with longer chain fatty acyl groups (than decanoyl) have been found to be substantially more effective as inhibitor of GCS. D-threo-1-phenyl-2-palmitoylamino-3-pyrrolidino-1-propanol (P4 or PPPP) analogues were first obtained by a Mannich reaction as described Abe, A. et al., *J. Biochem.*, 111, 191-196, 1992 or U.S. Pat. No. 5,916,911 and WO 2001004108.

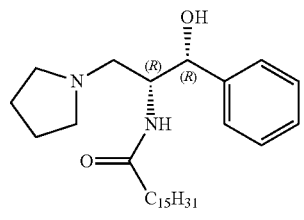

D-threo-P4

Preparation of D-threo-4'-hydroxy-P4, one of the most potent inhibitor of GCS, was described by Lee, L. et al., *J. Biol. Chem.*, 274, 21, 14662-14669, 1999. In addition, a series of dioxane substitutions was designed and tested. These included 3',4'-methylenedioxyphenyl-3',4'-ethylenedioxyphenyl-, and 3',4'-trimethylenedioxyphenyl-substituted homologues.

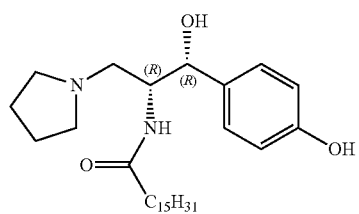

D-threo-4'-hydroxy-P4

Synthesis of enantiomerically pure D-threo-1-phenyl-2-benzyloxycarbonylamino-3-pyrrolidino-1-propanol (PBPP) and D-threo-P4 and its analogues from N-benzyloxycarbonyl-D-serine, was described by Jimbo M. et al, *J. Biochem.*, 127(3), 485-91, 2000 and EP 782992 (Seikagaku Kogyo Co.). PBPP is described as a potent GCS inhibitor.

Novel prodrugs of P4 derivatives were described in US 20020198240 and WO 2002062777.
Synthesis of enantiomerically pure of D-threo-ethylenedioxy-P4 and D-threo-p-methoxy-P4 were described by Husain A. and Ganem B., *Tetrahedron Lett.*, 43, 8621-8623, 2002. The key step is a highly syn-selective additions of aryl Grignard reagents to Garner aldehyde.

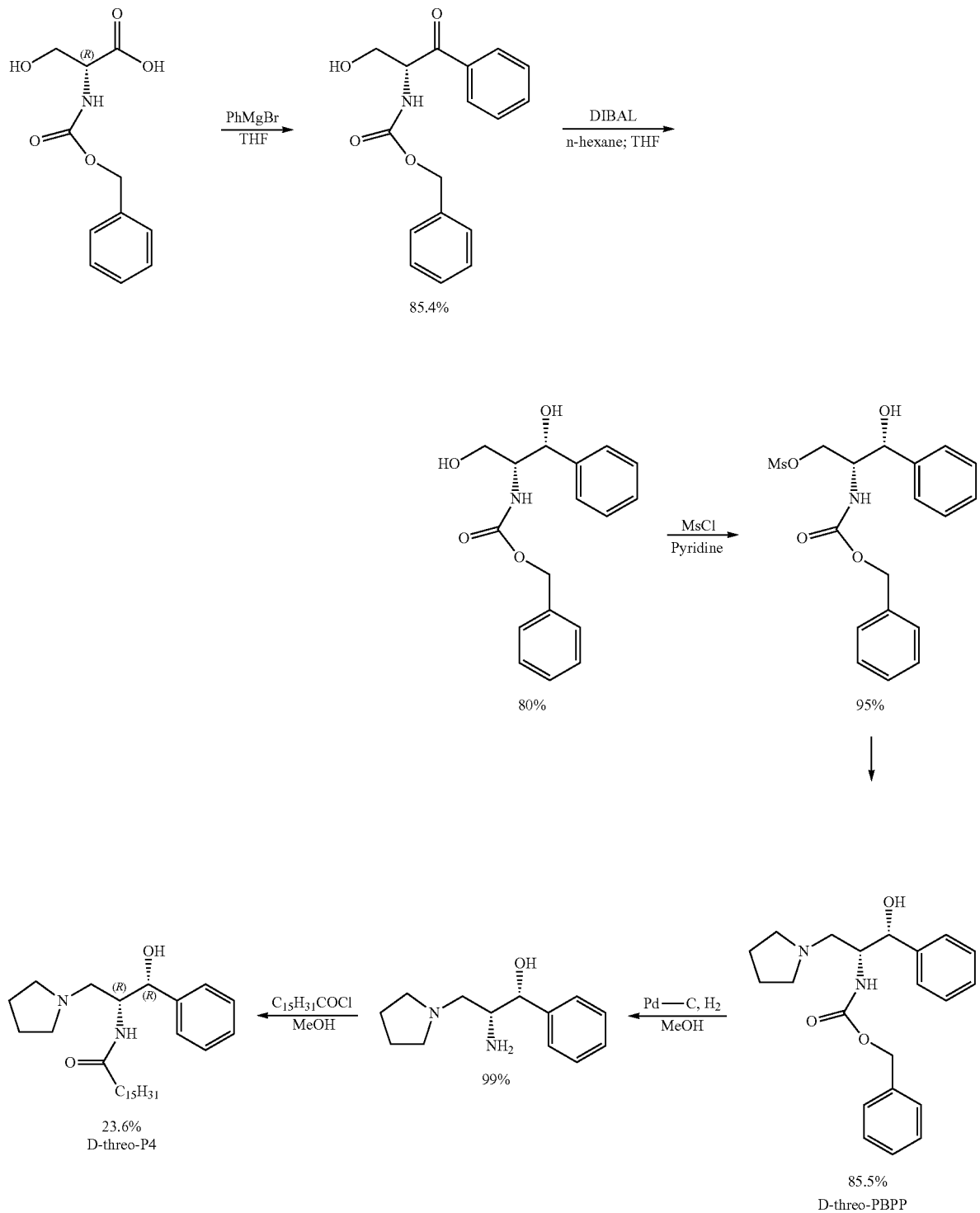

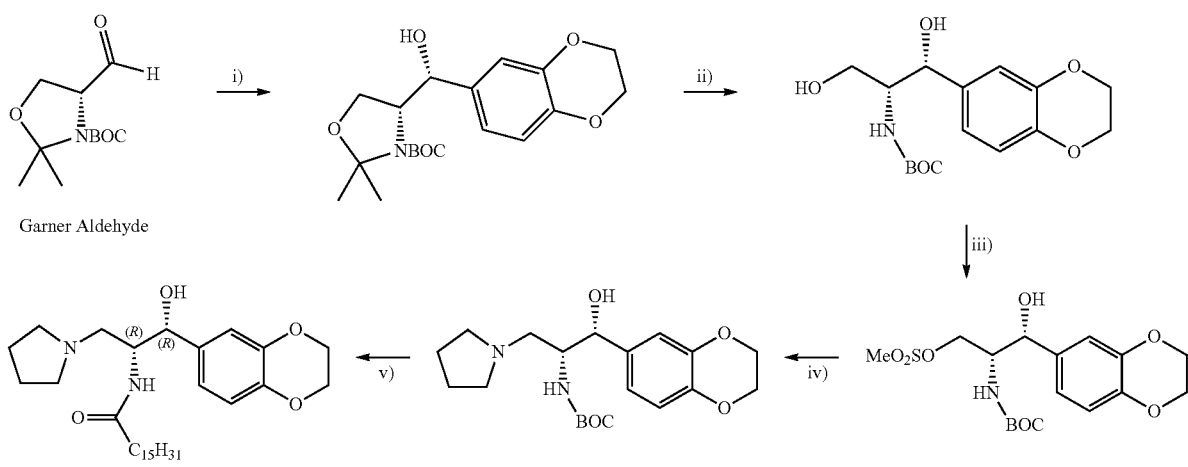

D-threo-ethylenedioxy-P4 i) 3,4-ethylenedioxyphenylmagnesium bromide, -78° C., CuI, THF: Me$_2$S, 64% ii) 0.1N HCl, THF 82%, MsCl, Et$_3$N, DCM, 0° C., 85% iii) pyrrolidine, DMF, 45° C., 58% iv) 3N HCl, 0° C., to RT then C$_{15}$H$_{31}$COCl, Et$_3$N, DMAP, DCM, -20° C., 87%

Diastereoselective synthesis of P4 analogues were described in U.S. Pat. No. 03/0,153,768 and WO 2003045928 (Genzyme Corp.); Oxazolines I [R1=(un)substituted aryl; R$^2$, R$^3$=H, (un)substituted aliphatic; NR$^2$R$^3$=heterocyclic] are prepared as intermediates for P4 glucosyltransferase inhibitors from R$^1$CHO and R$^2$R$^3$NCOCH$_2$CN. Thus, methyl isocyanoacetate CNCH$_2$CO$_2$Me was treated with pyrrolidine and the amide was treated with 1,4-benzodioxane-6-carboxaldehyde, followed by hydrolysis of the oxazoline using HCl in methanol, reduction of the keto group of amide II using LiAlH$_4$, and acylation with palmitoyl chloride to give D,L-threo-ethylenedioxy-P4 III.

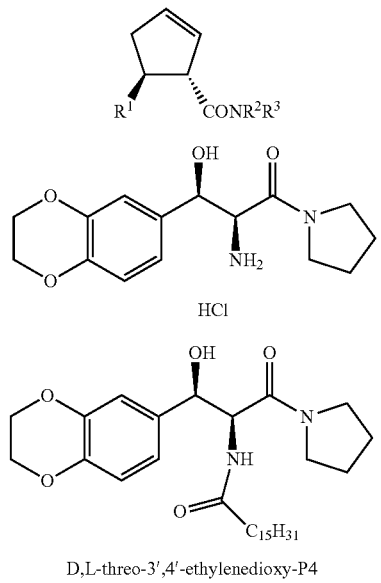

Synthesis of enantiopure P4 analogues were described in WO 2003008399 (Genzyme Corp.).

P4 derivatives, such as I [R$^1$,R$^5$=un(substituted) aromatic; R$^2$, R$^3$=H, un(substituted) aliphatic; NR$^2$R$^3$=(un)substituted non-aromatic heterocyclic ring; R$^4$=O, H$_2$], were prepared for their therapeutic use as GCS inhibitors. Thus, D-threo-ethylenedioxy-P4 was prepared via a multistep synthetic sequence starting from S-(+)-Ph glycinol, phenyl-α-bromoacetate, 1,4-benzodioxan-6-carboxaldehyde, pyrrolidine and palmitoyl chloride.

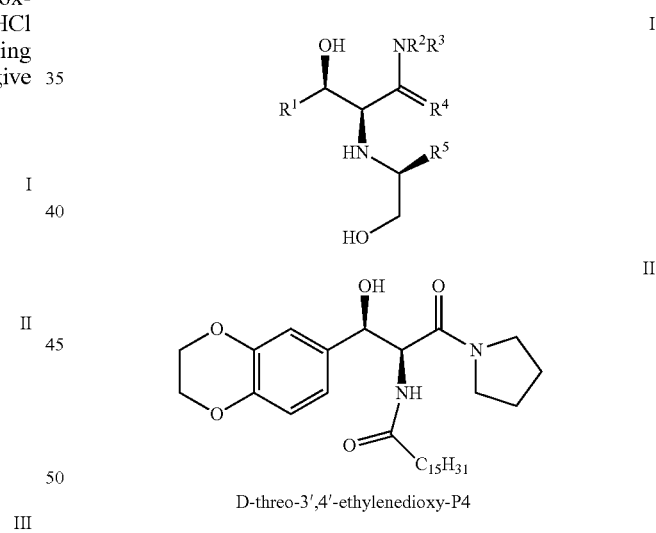

New D-threo-P4 analogues that bear ether substituents on the aromatic ring have been recently synthesized from D-serine and found to suppress neurite extension in an embryonic insect cell line as described by Slavish., J. P. et al., *Bioorg. Med. Chem. Lett.*, 14, 1487-1490, 2004.

Further references which serve as background to the present invention are U.S. Pat. Nos. 5,945,442; 5,952,370; 6,030,995 and 6,051,598; Journal of Labelled Compounds & Radiopharmaceuticals (1996), 38(3), 285-97; Published PCT application WO 01/38228; and Kastron et al. Latvijas PSR Zinatnu Akademijas Vestis, Kimijas Serija (1965) (4), 474-7.

Significantly, according to the best knowledge of the present inventors none of the compounds of the prior art which are structurally similar to the novel compounds of the present invention are known in the prior art as analgesics or immuno stimulants.

SUMMARY OF THE INVENTION

The present invention is directed to compounds of Formula 1

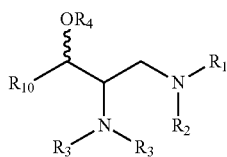

Formula 2 where $R_1$ is H or alkyl of 1 to 6 carbons, $R_2$ is H, alkyl of 1 to 6 carbons or the $R_1$ and $R_2$ groups together with the nitrogen form a saturated or unsaturated 4, 5, 6 or 7 membered ring that optionally includes one or two heteroatoms independently selected from N, O and S, said 4, 5, 6 or 7 membered ring optionally being substituted with a halogen, COOH, $CH_2OH$, OH, $B(OH)_2$, cyano or with an alkyl group having 1 to 6 alkyl groups;

$R_3$ is independently selected from H, alkyl of 1 to 20 carbons, aryl or heteroaryl, aryl-alkyl or heteroaryl-alkyl where the alkyl moiety has 1 to 4 carbons, cycloalkyl of 3 to 6 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons, or $R_3$ is CO—$R_7$ or CO—O—$R_7$ where $R_7$ is H, alkyl of 1 to 20 carbons, benzyl, alkyl of 1 to 20 carbons substituted with and $NH_2$ group, with a NHCOOalkyl or with an NH—COalkyl group where the alkyl group has 1 to 6 carbons, or $R_7$ is aryl, heteroaryl, aryl-alkyl or heteroaryl-alkyl where the alkyl moiety is branched or unbranched and has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons;

$R_4$ is H, alkyl of 1 to 6 carbons or CO—$R_8$ where $R_8$ is alkyl of 1 to 6 carbons;

the wavy lines represent bonds connected to carbons having R or S configuration, and $R_{10}$ is selected from the groups of formulas (i) and (ii)

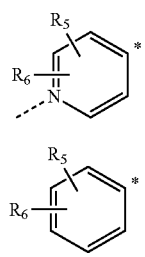

where the * indicates the carbon atom to which the remaining moiety of the molecule is attached;

$R_5$ and $R_6$ independently are H, alkyl of 1 to 6 carbons, halogen, alkoxy of 1 to 6 carbons or the $R_5$ and $R_6$ groups together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S, and said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons, with the proviso:

that when $R_{10}$ has formula (ii) then Formula 1 does not include compounds where $R_4$ is hydrogen and $R_1$ and $R_2$ jointly with the nitrogen form a morpholin or a pyrrolidin ring and where $R_5$ and $R_6$ both are H or one of $R_5$ and $R_6$ is $OCH_3$ and the other is H, and the present invention is also directed to all pharmaceutically acceptable salts of said compounds.

The present invention is also directed to pharmaceutical compositions containing the above-noted novel compound to be used as analgesics and/or immuno stimulants in mammals, and to methods of using said pharmaceutical compositions as analgesics and/or as immuno stimulants.

DETAILED DESCRIPTION OF THE INVENTION

A general description of the compounds of the invention is provided in the Summary Section of the present application for patent. Most compounds of the invention contain one or more asymmetric centers, such that the compounds may exist in enantiomeric as well as in diastereomeric forms. In fact, most of the compounds of the present invention have two asymmetric carbons adjacent to one another and therefore can exist in erythro or threo form, with each of these two forms having dextrorotatory (D) or levorotary (L) enantiomers. Although the threo form is generally preferred in accordance with the present invention for analgesic activity, unless it is specifically noted otherwise, the scope of the present invention includes all enantiomers, diastereomers and diastereomeric and racemic mixtures. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" (or "(+/−)" or "(±)") appears it also includes the enantiomeric form (mirror image) of the structure actually shown in the formula.

For Example:

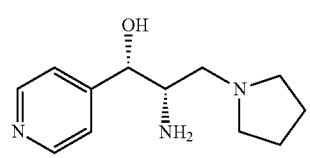

DL-threo or ±-threo

Thus, in the example above, only one enantiomer is shown, but because the designation "DL" (or "(+/−)" or "(±)") appears below the formula, its optical isomer

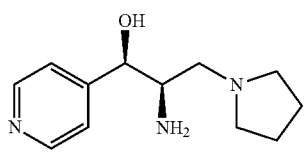 [SMILES: N[C@H](CN1CCCC1)[C@H](O)c1ccncc1]

and all racemic mixtures of the two optical isomers are also included.

In the case of some compounds of the present invention one enantiomer of the threo, and in some cases of the erythro, is significantly more active as an analgesic or immuno stimulant than the other enantiomer of the same pair. For this reason the isolated enantiomer which is significantly more active than the other is considered a novel and inventive composition even if the racemic mixture or one single enantiomer of the same compounds have already been described in the prior art.

Some of the novel compounds of the present invention may contain three or more asymmetric centers.

Keeping the foregoing examples in mind a person of ordinary skill in the art should readily understand the scope of each described example, although in a broad sense all isomers, enantiomers and racemic mixtures are within the scope of the invention.

The term "alkyl" in the general description and definition of the compounds includes straight chain as well as branch-chained alkyl groups.

Generally speaking the compounds of the invention may form salts with pharmaceutically acceptable acids or bases, and such pharmaceutically acceptable salts of the compounds of Formula 1 are also within the scope of the invention.

Referring now to the novel compounds of Formula 1, the $R_5$ and $R_6$ groups preferably both are independently selected from H, alkyl, alkoxy and still more preferably are H. In the preferred compounds the $R_3$ groups are preferably both H, or one of the $R_3$ groups is H and the other is an acyl group or an arylalkylcarbamoyl group. The $R_4$ group is preferably H (but see the "proviso" in the Summary section) or alkanoyl, and the $R_1$ and $R_2$ groups preferably are pyrrolidino or morpholino.

The presently most preferred novel compounds of the invention are disclosed with their structural formulas in the ensuing Table and/or description, showing activity of exemplary compounds relevant to their ability to act as analgesics.

Biological Activity, Modes of Administration

The novel compounds of the invention have analgesic and/or immunostimulant activity in mammals. Some of the compounds described in the introductory section which per se are known in the art have been discovered by the present inventors to also have analgesic effect in mammals. To the best of the knowledge of the present inventors the analgesic or immunostimulant biological activity of the known compounds was not known before the present discovery.

An art-accepted model or assay for measuring an analgesic effect of a compound in chronic pain (in particular peripheral neuropathy) is the model known as Kim and Chung 1992, Pain 150, pp 355-363 (Chung model). This model involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to low-threshold mechanical stimuli and will perceive pain instead of the faint sensation of touch. This sensitivity to normally non-painful touch, called "tactile allodynia", develops within the first week after surgery and lasts for at least two months. The allodynia response includes lifting the affected hindpaw to escape from the stimulus, licking the paw and holding it in the air for many seconds. None of these responses is normally seen in the control group.

To produce the tactile allodynia, rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

After a complete hemostasis is confirmed, the wounds are sutured. A small amount of antibiotic ointment is applied to the incised area, and the rat is transferred to the recovery plastic cage under a regulated heat-temperature lamp.

On the day of the experiment, at least seven days after the surgery, typically six rats per test group are administered the test drugs by intraperitoneal (i.p.) injection or oral gavage (p.o.). For i.p. administration, the compounds are formulated in $H_2O$ and given in a volume of 1 ml/kg body weight by injecting into the intraperitoneal cavity. For p.o. administration, the compounds are formulated in $H_2O$ and given in a volume of 1 ml/kg body weight using an 18-gauge, 3 inch gavage needle that is slowly inserted through the esophagus into the stomach.

Tactile allodynia is assessed via von Frey hairs, which are a series of fine hairs with incremental differences in stiffness. Rats are placed in a plastic cage with a wire mesh bottom and allowed to acclimate for approximately 30 minutes. To establish the pre-drug baseline, the von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., Ann. Rev. Pharmacol. Toxicol. 20:441-462 (1980) hereby incorporated by reference. Tactile allodynia is measured prior to and 15, 30, and 60 minutes after drug administration. The post-drug threshold is compared to the pre-drug threshold and the percent reversal of tactile sensitivity is calculated based on a normal threshold of 15.1 grams.

Table 1 below indicates the degree of pain reversal obtained in the Chung model with exemplary compounds of the invention. The intraperitonial (i.p.) and/or intravenous (iv) administration of the compounds was in doses ranging from 1 µg/kg to 300 µg/kg or 3 mg/kg PO and the peak percentage of reversal of allodynia was measured at 15, 30 or 60 minutes after administration, as is indicated in the table. Data are expressed as the highest % allodynia reversal (out of 3 time points: 15 min, 30 min, or 60 min. post-drug) with a minimum of a 20% allodynia reversal in the rat Chung model. Comparisons between groups (drug treated vs. saline treated) were made using a two-tailed, 2-sample, unpaired t-test. Compounds that are not shown which were not statistically analgesic following an IP dose of 300 ug/kg, but may still be analgesic. Compounds that do not exhibit significant analgesia at 100 mg/kg are not considered to be analgesic.

TABLE 1

| Compound # | Chemical Formula | Peak % Pain reversal: time post dose | Dose µg/kg, Mode of administ. |
|---|---|---|---|
| 1 | 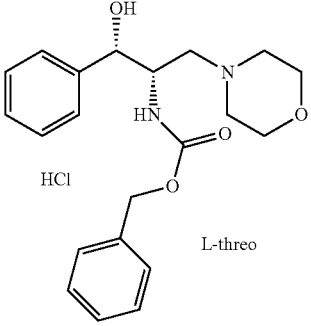 [SMILES: O=C(N[C@@H](CN1CCOCC1)[C@@H](O)c1ccccc1)OCc1ccccc1 ; Cl] L-threo | 44% 30 min | 300 µg/kg IP |
| 3 | 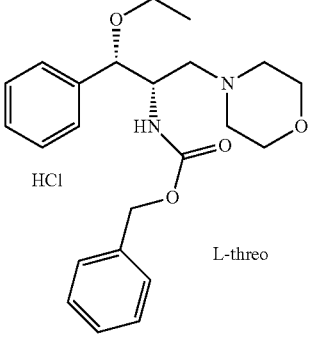 L-threo | 92% 60 min | 300 µg/kg IP |
| 46 | 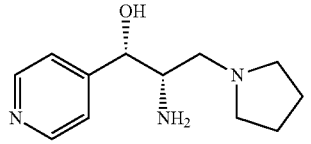 DL-threo | 96% 60 min | 30 µg/kg IP |

An art accepted method for measuring immuno stimulation comprises systemic administration of compounds to assay for the ability to stimulate the immune system, possibly due to nonspecific upregulation of the hemolymphoreticular system. This upregulation could result in increased numbers of lymphocytes of both T- and B-cell lineage. Although applicant does not wish to be bound by the biological theory of the immuno stimulation, actual immunostimulatory efficacy of the compounds can be demonstrated in vivo by assaying splenic size in response to administration of the test compound to laboratory test species rats. Generally speaking any compound that exhibits splenic enlargement following dosing of 200 mg/kg or less may be considered an immunostimulant.

Modes of Administration:

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. For human adults such doses generally will be in the range 0.1-5000 mg/day; more preferably in the range 1 to 3000 mg/day, still more preferably in the range of 10 mg to 1000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery. Another aspect of the invention is drawn to therapeutic compositions comprising the novel compounds of the invention and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more of the novel or otherwise known compounds of the invention, or of pharmaceutically acceptable salts thereof to a mammal in need thereof. As indicated above, the compound will usually be formulated in a form consistent with the desired mode of delivery.

Compounds of the invention which are immuno stimulants are administered subject to the same basic principles as the compounds having analgesic activity, in doses which are best determined on a case-by-case and/or species-by-species and, in case of humans, at times on a patient-by-patient basis. Generally speaking the effective dose will be in the range of 10 ng/kg to 200 mg/kg.

Synthetic Methods for Obtaining the Compounds of the Invention, Experimental

The compound of the invention can be synthesized by utilizing the synthetic methods described in the experimental below, or such modifications of the below described experimental methods which will become readily apparent to those skilled in the art in light of the present disclosure.

General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 nm, C18, 4.5×50 mm)

The HPLC method used was a gradient of 5% solvent B to 100% in 7 min. Solvent A was $H_2O$ with 0.05% TFA and solvent B was $CH_3CN$ with 0.05% TFA (Method A).

Melting points were measured with a Büchi B-545 melting point apparatus and were uncorrected. To isolate reaction products the solvent were removed by evaporation using a vacuum rotatory evaporator, the water bath temperature not exceeding 40° C.

General Synthetic Routes

The compound of the invention can be synthesized by utilizing the synthetic methods described in a general sense immediately below and in more detail in the experimental section of the present application, or by such modifications of the below described general and experimental methods which will become readily apparent to those skilled in the art in light of the present disclosure.

A general synthetic route to the compound of the present invention which are substituted "1-hydroxyl-propyl amines" may lead through the synthesis of the corresponding substituted "3-hydroxyl-propyl amide" compounds, followed by reduction of the carbonyl group of the "carboxylic acid amide" moiety with a reducing agent such as lithium aluminum hydride, or like reducing agent.

General Synthetic Scheme A

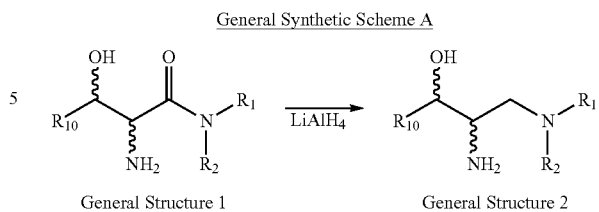

General Structure 1            General Structure 2

This reaction is illustrated in General Synthetic Scheme A, where, generally speaking, the variables have the meaning described in the Summary Section of the present application for patent. A person of ordinary skill in the art of organic synthesis will nevertheless readily understand that depending on the nature of the substituents designated $R_1$, $R_2$ and $R_{10}$ certain groups may need to be protected for the performance of the reduction step.

The substituted "3-hydroxyl-propyl amide" compounds can, generally speaking, be synthesized as described below in the following General Reaction Scheme 1 and General Reaction Scheme 2.

General Reaction Scheme 1

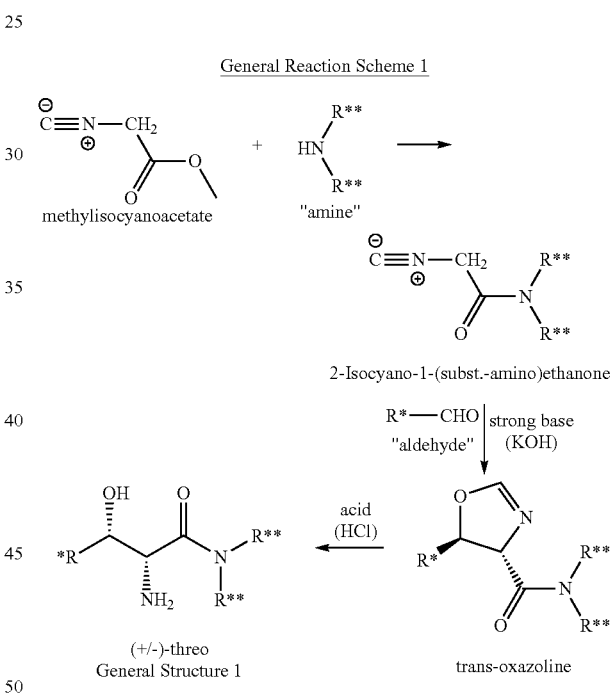

Thus, in accordance with General Scheme 1, methyl isocyanoacetate (or ethyl isocyanoacetate available commercially) is reacted with an "amine" which includes the $R_1$ and $R_2$ groups to provide the 2-isocyanoacetic acid amide derivative shown in General Reaction Scheme 1. Typical examples for the amines used in the reaction are pyrrolidine, piperidine, azetidine, morpholine, 2,5-dihydro-1H-pyrrole, dialkylamines such as diethylamine, 3-fluoro-, 3,3-difluoro or 3-hydroxy substituted pyrrolidines. The 2-isocyanoacetic acid amide derivative is then reacted in methanol in the presence of base (such as KOH) with an "aldehyde" which includes the $R_{10}$ group to provide a trans "oxazoline" with high diastereoselectivity (trans:cis ratios generally >97:3) as shown in General Reaction Scheme 1. The trans oxazoline is then treated in methanol with a strong acid, such as HCl, to open the ring and to provide the threo-3-substituted-3-hydroxy-2-amino-propionic acid amide intermediates (with a threo:erythro ratios generally >97:3) as shown in General Reaction Scheme 1.

Compounds of Formula 1 and/or of General Structure 1, where the amino group of formula $NHR_1R_2$ is a weaker nucleophile, such as indoline, thiomorpholine and the like, can be made as illustrated in Reaction Scheme 2 for the synthesis of intermediate compounds (±)-threo-2-amino-3-hydroxy-1-(indolin-1-yl)-3-(pyridin-4-yl)propan-1-one dihydrochloride Compound 243 and (±)-threo-2-amino-3-hydroxy-1-(thiazolidin-3-yl)-3-(pyridin-4-yl)propan-1-one dihydrochloride Compound 242.

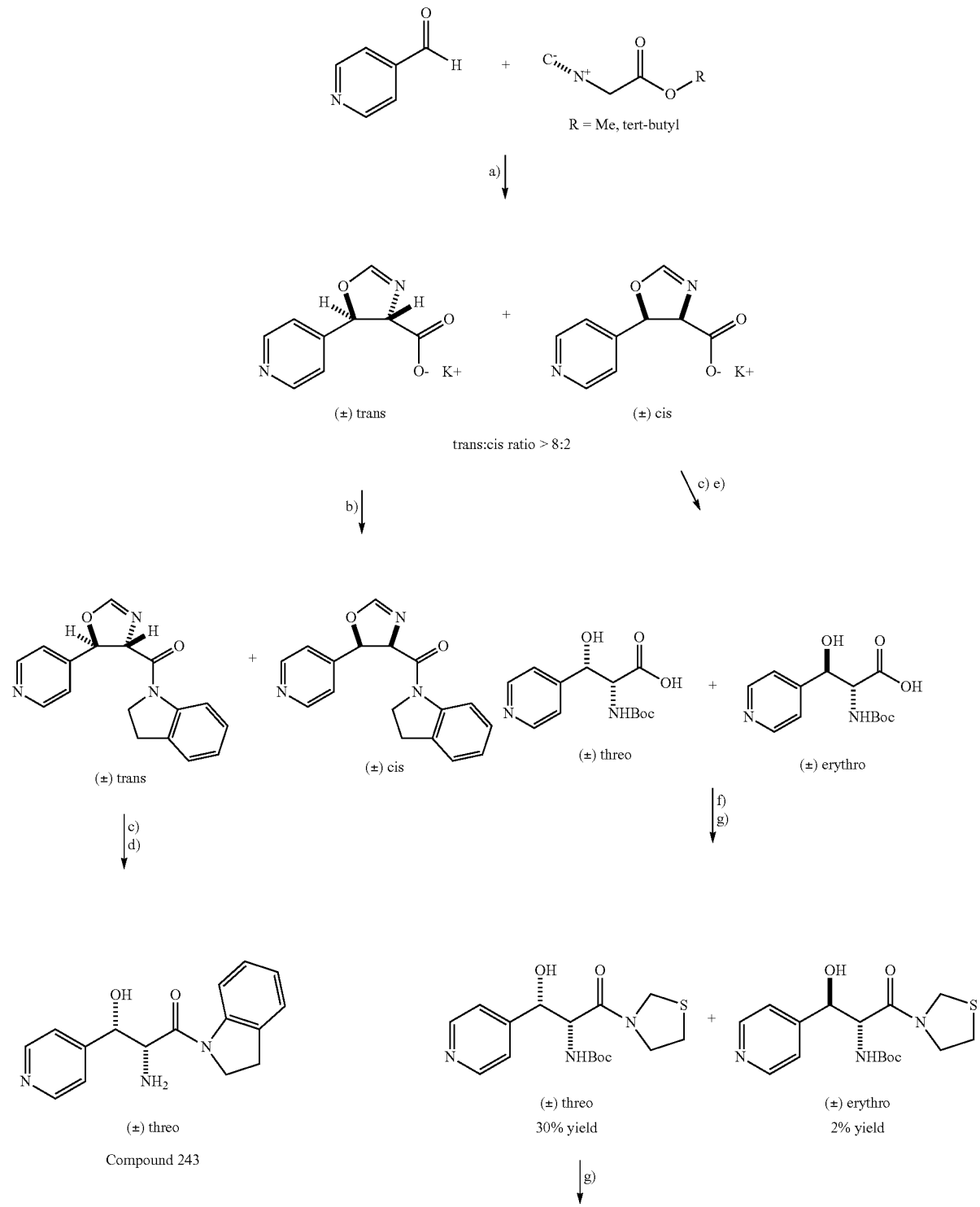

-continued

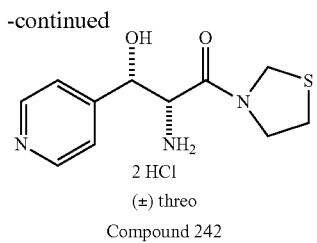

2 HCl (±) threo

Compound 242 a) KOH, MeOH; b) Indoline, EDCl, TEA, HOBT, CH$_2$Cl$_2$. c) HCl (1M) in MeOH d) i. Silica Gel Chromatography. ii HCl (0.1M) in i-PrOH e) BOC$_2$O, NaOH, Dioxane. f) Thiazoldine, EDCl, TEA, HOBT, CH$_2$Cl$_2$; g) Silica Gel Chromatography g) HCl (1M) in MeOH.

In Reaction Scheme 2 EDC1 stands for 1-(3-dimethylaminopropyl)-ethylcarbodiimide hydrochloride; HOBT stands for 1-hydroxybenzotriazole; BOC$_2$O stands for di-t-butyldicarbonate and TEA stands for triethylamine Compounds 242 and 243 can be reduced, as illustrated in General Synthetic Scheme A to provide compounds of the invention.

Another general synthetic route may follow in general terms the synthesis of Compound 1, Compound 2 and Compound 3, specifically described in detail in the experimental section below, modified with such modifications which in light of the present disclosure will become readily apparent to a person of ordinary skill in the art.

Isomerically pure and/or enantiomerically pure compounds and further derivatives of the 3-substituted-3-hydroxy-2-amino-propionic acid amide intermediates or of the substituted 1-hydroxy propylamines of the invention are obtained by separation techniques and reactions which, per se, are well known to the synthetic chemist. Some of the typical separation techniques and reactions are generally described below.

Separation of threo and erythro isomers, when both are formed in the reactions leading to the compounds of the invention, can typically be performed by chromatographic methods. The chromatographic separation may occur the level of the substituted 3-hydroxyl-propionic acid amide intermediate compounds or at the level of the substituted 1-hydroxylpropyl amine compounds of the invention.

The more abundantly formed threo isomers can also be converted into the erythro isomers by oxidizing to the ketone level the hydroxyl group in the 3 position of the propanoic acid moiety and subsequently reducing the resulting ketone to the hydroxyl level in the intermediate 3-substituted-3-hydroxy-2-amino-propionic acid amide compounds or in the compounds of the invention.

Separation of enantiomeric mixtures can be performed on Chiralpak columns which are well known in the art.

The amino function in the 2-position of the propyl amine moiety is, generally speaking, more reactive towards acylation and carbamoylation than the hydroxyl group in the 1 position. Therefore, acylated derivatives of the 2-amino function can be prepared by using acyl chlorides such as acetyl chloride and hexanoyl chloride. Or the 1-hydroxy and 2-amino groups of the compounds of the invention can be acylated in the same reaction. Carbamate derivatives of the 2-amino function can be obtained by using chloroformates, such as benzylchloroformate. A tertiary butyl carbamoyl function or benzyl-carbamoyl function can also serve as a removable protecting group of the 2-amino function.

Alkylation of the 2-amino function can be performed by condensing the compound bearing the 2-NH$_2$ group with an aldehyde to obtain a Schiff base intermediate which can be reduced, without isolation, to provide the N-alkyl, arylalkyl or heteroaryl-alkyl compounds of the invention.

Detailed Description of the Synthesis of Preferred Compounds (Experimental)

Preparation of D-threo-2-amino-3-morpholino-1-phenylpropan-1-ol dihydrochloride Compound 4

(R)-Methyl 1-((S)-1-phenylethyl)aziridine-2-carboxylate EBE 06044B

To solution of methyl 2,3-dibromopropionate (25 mL, 198 mmol) in toluene at 5° C. was added triethylamine (55 mL, 0.39 mmol) in toluene (100 mL). After stirring for 5 min (S)-(1)-phenethylamine (25 mL, 198 mmol) in toluene (100 mL) was added dropwise. The suspension was refluxed for 3 h and allowed to cool down, filtered and the volatiles were evaporated under reduced pressure to give a residue that was purified by column chromatography (950 g of silica gel) with a gradient of 0-20% EtOAc in cyclohexane to yield to (S)-methyl 1-((S)-1-phenylethyl)aziridine-2-carboxylate EBE 06044A as a yellow oil (17.31 g, 43% yield) and (R)-methyl 1-((S)-1-phenylethyl)aziridine-2-carboxylate EBE 06044B as a yellow oil (15.14 g, 37% yield).

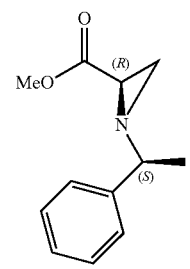

EBE 06044B

MW: 205.3; Yield EBE 06044B: 37%; Yellow Oil. Yield: EBE 06044A: 43%, Yellow Oil.

R$_f$: EBE 06044A=0.5; R$_f$: EBE 06044B=0.35 (EtOAc:cyclohexane=25:75).

$^1$H-NMR (CDCl$_3$,) EBE 06044A: 1.47 (d, 3H, J=6.6 Hz, CH$_3$), 1.60 (d, 1H, J=6.4 Hz, CH), 2.13 (d, 1H, J=2.6 Hz), 2.21 (dd, 1H, J=3.2 Hz, J=6.4 Hz), 2.54 (q, 1H, J=6.6 Hz), 3.75 (s, 3H, OCH$_3$) 7.23-7.40 (m, 5H, ArH).

$^1$H-NMR (CDCl$_3$,) EBE 06044B: 1.46 (d, 3H, J=6.6 Hz, CH$_3$), 1.79 (d, 1H, J=6.6 Hz, CH), 2.08 (d, 1H, J=3.11 Hz, 6.6

Hz), 2.34 (dd, 1H, J=3.1 Hz, J=1.0 Hz), 2.56 (q, 1H, J=6.6 Hz), 3.67 (s, 3H, OCH$_3$) 7.24-7.36 (m, 5H, ArH).

$^{13}$C-NMR (CDCl$_3$,) EBE 06044B: 23.5, 35.0, 36.9, 52.2, 69.8, 126.5, 127.2, 128.5, 143.6, 171.1.

HPLC: Method A, detection at 254 nm, EBE 06044B RT=6.11 min, peak area 92.9%.

((R)-1-((S)-1-Phenylethyl)aziridin-2-yl)methanol EBE 06046

A 250 mL round bottom flask was charged with anhydrous THF (100 mL) and LiAlH$_4$ (2.77 g, 73.1 mmol). While the suspension is stirred at 0° C., a solution of (S)-methyl 1-((S)-1-phenylethyl)aziridine-2-carboxylate EBE 06044B (10.0 g, 48.7 mmol) in THF (50 mL) was added dropwise over 20 min. The dropping funnel was washed with THF (2×3 mL) and allowed to react 20 min at 0° C. Maintaining the reaction mixture at 0° C., a solution of KOH (10%, 20 mL) was added dropwise for 20 min (caution the reaction is exothermic). The mixture was stirred for 0.5 h at 25° C. and the white precipitate removed by filtration through a celite pad that was washed with diethyl ether (30 mL). The combined organic filtrates were washed with NaH$_2$PO$_4$ and the aqueous layer was extracted with Et$_2$O (3×30 mL). The combined organic phase were dried with Na$_2$SO$_4$ and concentrated to give ((R)-1-((S)-1-phenylethyl)aziridin-2-yl)methanol EBE 06046 as a white solid (10.4 g, 90% yield).

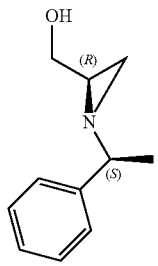

EBE 06046

MW: 177.2; Yield: 90%; White Solid; Mp (° C.): 37.7.

$^1$H-NMR (CDCl$_3$,): 1.43 (d, 3H, J=6.6 Hz, CH$_3$), 1.49 (d, 1H, J=6.5 Hz, CH), 1.65-1.71 (m, 1H, CH), 1.92 (d, 1H, J=3.5 Hz, NCH), 2.26 (s, 1H, OH), 2.53 (q, 1H, J=6.6 Hz, NCH), 3.32-3.37 (m, 1H, OCH$_2$), 3.56 (m, 1H, OCH$_2$), 7.23-7.35 (m, 5H, ArH).

$^{13}$C-NMR (CDCl$_3$,): 22.9, 31.4, 39.3, 62.5, 69.4, 126.6, 127.3, 128.6, 144.5.

(R)-1-((S)-1-Phenylethyl)aziridine-2-carbaldehyde EBE 06048

A three neck, 250 mL round bottom flask was equipped with a low temperature thermometer and two (2) equalizing dropping funnels. One of these was connected to a nitrogen line and charged with a solution of ((R)-1-((S)-1-phenylethyl) aziridin-2-yl)methanol EBE 06046 (7.0 g, 39.5 mmol) in CH$_2$Cl$_2$ (75 mL), the other was charged with a solution of DMSO (9.25 g, 118.5 mmol) in CH$_2$Cl$_2$ (11 mL). To a solution of oxalyl chloride (7.5 g, 59.3 mmol) in CH$_2$Cl$_2$ (90 mL) under N$_2$ at −78° C., the DMSO solution was added dropwise during 20 min and stirred for 20 min. EBE 06046 (7.0 g, 39.5 mmol) in CH$_2$Cl$_2$ (75 mL) was added dropwise over 50 min. then the dropping funnel was charged with DIEA (42.6 mL, 237 mmol) in CH$_2$Cl$_2$ (10 mL) and the reaction mixture was stirred for 30 min at −45° C. The DIEA solution was added over 5 min with the reaction mixture at −78° C. and the reaction was allowed to warm to room temperature. The reaction mixture was washed with H$_2$O (3×50 mL), dried over MgSO$_4$, filtered, evaporated. The crude product obtained was purified by column chromatography on silica with a gradient of 0-20% [v/v] EtOAc in cyclohexane to give (R)-1-((S)-1-phenylethyl)aziridine-2-carbaldehyde EBE 06048 as a yellow oil (5.59 g, 81% yield).

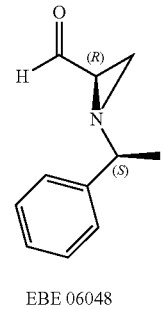

EBE 06048

MW: 175.2; Yield: 81%; Yellow Oil.

R$_f$: EBE 06048: 0.3 (EtOAc:cyclohexane=20:80).

$^1$H-NMR (CDCl$_3$,): 1.47 (d, 3H, J=6.6 Hz, CH$_3$), 1.94 (d, 1H, J=6.7 Hz, NCH$_2$), 2.08 (dt, J=2.9 Hz, J=6.4 Hz, NCH), 2.37 (d, 1H, J=2.6 Hz, NCH$_2$), 2.61 (q, 1H, J=6.6 Hz, NCH), 7.20-7.38 (m, 5H, ArH), 8.92 (d, 1H, J=6.2 Hz).

$^{13}$C-NMR (CDCl$_3$,): 22.7, 32.1, 43.2, 68.1, 125.5, 126.5, 127.6, 142.4, 198.7.

(R)-Phenyl((R)-1-((S)-1-phenylethyl)aziridin-2-yl) methanolEBE 06066

To a solution of bromobenzene (4.93 g, 31.4 mmol) in THF 125 mL under nitrogen at −78° C. was added t-BuLi (1.7 M in pentane, 50 mL). The mixture was stirred for 0.5 h at room temperature. The mixture was cooled down to −78° C. and a solution of (R)-1-((S)-1-phenylethyl)aziridine-2-carbaldehyde EBE 06048 (2.5 g, 14.3 mmol) in THF (16.7 mL) at −78° C. was added dropwise. The reaction mixture was treated with H$_2$O (20 mL), the organic layer was separated and the aqueous phase was extracted with EtOAc. The combined organic layers were dried over MgSO$_4$, filtered and concentrated in vacuo to give a residue that was purified by column chromatography using a gradient of 0-20% [v/v] EtOAc in cyclohexane to give (R)-phenyl((R)-1-((S)-1-phenylethyl) aziridin-2-yl)methanol EBE 06066 (3.13 g, 86% yield).

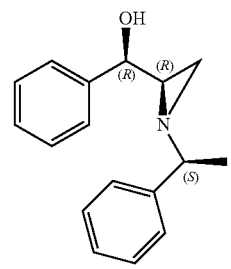

EBE 06066

MW: 253.3; Yield: 86%.

R$_f$: =0.3 (EtOAc:cyclohexane=20:80).

$^1$H-NMR (CDCl$_3$,): 1.47 (d, 3H, J=6.6 Hz, CH$_3$), 1.57 (d, 1H, J=6.5 Hz, CH), 1.79 (dt, 1H, J=3.5 Hz, J=8.7 Hz, CH), 2.04 (d, 1H, J=3.5 Hz, OCH), 2.35 (bs, 1H, OH), 2.53 (q, 1H,

J=6.5 Hz, CH), 4.23 (d, 1H, J=5.7 Hz, OCH), 7.07-7.13 (m, 2H, ArH), 7.16-7.20 (m, 3H, ArH), 7.24-7.34 (m, 5H, ArH).

$^{13}$C-NMR (CDCl$_3$,): 22.4, 32.0, 44.6, 69.4, 74.1, 125.8(2× C), 126.9 (2×C), 127.3, 127.6, 128.2 (2×C), 128.7 (2×C), 142.0, 144.2.

[ ]$^{22}_D$=−71.53 (c=0.59, CHCl$_3$).

D-threo-2-((S)-1-Phenylethylamino)-3-morpholino-1-phenylpropan-1-ol dihydrochloride Compound 5

To a solution of (R)-phenyl((R)-1-((S)-1-phenylethyl) aziridin-2-yl)methanol EBE 06066 (1.5 g, 5.92 mmol) in CH$_3$CN (19 mL) at RT was added iodotrimethylsilane (3.55 g, 17.8 mmol). The solution was stirred for 2 h and morpholine (1.032 g, 11.84 mmol) was added. After 2 h at reflux, the reaction mixture was treated with HCl (1M) to reach pH=1 and stirred for 10 min. After a slow addition of NaHCO$_3$ to reach pH=9, the product was extracted with EtOAc, dried over Na$_2$SO$_4$, filtered to give after evaporation a crude brown oil that was purified by column chromatography using a gradient of 0-20% [v/v] MeOH in EtOAc to give D-threo-2-((S)-1-phenylethylamino)-3-morpholino-1-phenylpropan-1-ol EBE 06068A (0.831 g, 42%) as a pale brown solid. To a solution of D-threo-2-((S)-1-phenylethylamino)-3-morpholino-1-phenylpropan-1-ol EBE 06068A (0.100 g, 0.294 mmol) in ethanol (1 mL) was added a solution of HCl (0.8 M, 0.816 mL) in EtOH. Evaporation of the volatiles afforded to D-threo-2-((S)-1-phenylethylamino)-3-morpholino-1-phenylpropan-1-ol dihydrochloride Compound 5 as white solid (0.125 g, 100%).

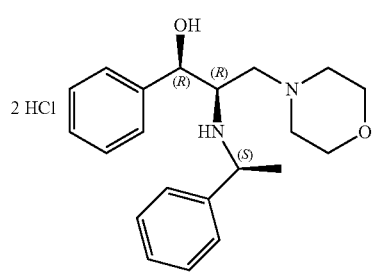

Compound 5

MW: 412.37; Yield: 42%; White Solid; Mp (° C.): 157.2 (dec).

R$_f$: 0.3 (MeOH:EtOAc=20:80) EBE 06068A.

$^1$H-NMR (CD$_3$OD,): 1.19 (t, 2H, J=7.0 Hz, NCH$_2$), 1.71 (d, 3H, J=6.8 Hz, CH$_3$), 3.45 (m, 2H, J=7.1 Hz, NCH$_2$), 3.62 (q, 2H, J=7.1 Hz, N—CH$_2$), 3.97 (t, 4H, J=4.5 Hz, OCH$_2$), 4.06 (m, 1H, CH—N), 4.75 (q, 1H, J=6.8 Hz, CH—N), 5.21 (d, 1H, J=5.1 Hz, CH—O), 7.44-7.56 (m, 10H, ArH).

MS-ESI m/z (% rel. Int.): 341.1 ([MH]$^+$, 20).

$^{13}$C-NMR (CD$_3$OD,): 24.4, 54.5 (2×C), 55.5, 55.9, 60.0, 67.0 (2×C), 75.6, 126.3 (2×C), 126.5 (2×C), 127.0, 127.1, 128.1 (2×C), 128.5 (2×C), 142.2, 145.3.

HPLC: Method A, detection at 254 nm, Compound 5 RT=4.41 min, peak area 99%.

Threo-2-Amino-3-morpholino-1-phenylpropan-1-oldihydrochloride Compound 4

To a solution of D-threo-2-((S)-1-phenylethylamino)-3-morpholino-1-phenylpropan-1-ol EBE 06068A (0.400 g, 1.17 mmol) in MeOH (6 mL) at RT was added acetic acid (0.133 mL, 2.35 mmol). The reaction vessel was flushed with nitrogen and Pd(OH)$_2$ (25% weight, 0.150 g) was added. The nitrogen atmosphere was exchanged with hydrogen using three cycle of vacuum and hydrogen addition using a balloon of hydrogen. After stirring for 16 h under hydrogen the reaction mixture was filtrated through celite to give EBE 06070A the acetate salt of (2R)-amino-3-morpholin-4-yl-(1R)-phenyl-propan-1-ol (0.279 g, 98% yield). To as solution of EBE 06070A the acetate salt of (2R)-amino-3-morpholin-4-yl-(1R)-phenyl-propan-1-ol (0.100 g, 0.338 mmol) in ethanol (1 mL) was added a solution of HCl (0.8 M, 0.930 mL) in EtOH. Evaporation of the volatiles afforded to D-threo-2-amino-3-morpholino-1-phenylpropan-1-ol dihydrochloride Compound 4 (0.104 g, 100% yield) as an off white solid. (Adapted from Shin, S—H.; Han, E. Y.; Park, C. S.; Lee, W. K.; Ha, H.-J. *Tetrahedron Asymmetry*, 2000, 11, 3293-3301).

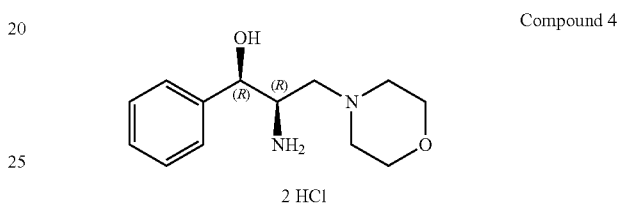

Compound 4

MW: 309.23; Yield: 99%; Off White Solid; Mp (° C.): 183.4.

$^1$H-NMR (CD$_3$OD,): 3.30-3.77 (m, 6H, CH$_2$N), 3.92-4.05 (m, 4H, CH$_2$O), 4.05-4.16 (m, 1H, CH), 4.85-4.98 (m, 1H, CH), 7.35-7.60 (m, 5H, ArH).

$^{13}$C-NMR (CD$_3$OD,): 53.2, 58.3, 58.5 (2×C), 64.9 (2×C), 72.6, 128.0 (2×C), 130.2 (2×C), 140.3.

MS-ESI m/z (% rel. int.): 237.1 (100, [MH]$^+$).

HPLC: Isocratic 10% CH$_3$CN in H$_2$O (pH 10, [NH$_4$OH]=5 mM), detection UV 254 nm, Compound 4 RT=6.63 min, peak area 97.3%.

[ ]$^{22}_D$=−10.7 (c=1.00, MeOH).

Preparation of Benzyl L-threo-1-hydroxy-3-morpholino-1-phenylpropan-2-ylcarbamate hydrochloride Compound 1

Benzyl (S)-3-hydroxy-1-oxo-1-phenylpropan-2-ylcarbamate TTA 08010B

To a stirred solution of Z-L-Ser-OH (6.00 g, 25.08 mmol) in 32 mL of anhydrous THF at 0° C. under nitrogen was added dropwise 1 M phenylmagnesium bromide in THF (32 mL, 200 mmol). (The symbol Z designates a benzylcarbamoyl group). The mixture was stirred 15 h at RT under nitrogen. A solution of 2 M HCl (100 mL) was slowly added at 0° C. and the mixture was partitioned between ethyl acetate (750 mL) and acidic water. The organic layer was washed with water (2×20 mL), 1 N aqueous sodium bicarbonate (2×20 mL), brine (2×20 mL) and dried over MgSO$_4$. After removing ethyl acetate by evaporation at 30-35° C., the crude product (4.50 g, 60% yield) was cristallized in a mixture of ethyl acetate: hexane=25 mL:20 mL to give benzyl (S)-3-hydroxy-1-oxo-1-phenylpropan-2-ylcarbamate TTA 08010B as a white solid (1.40 g, 20% yield).

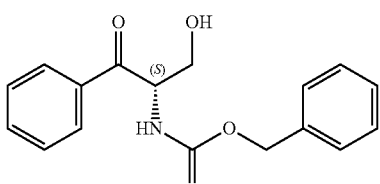

TTA 08010B

MW: 299.32; Yield: 20%; White Solid; Mp (° C.): 106.5. $R_f$: 0.75 (CH$_2$Cl$_2$:MeOH=9:1).

$^1$H-NMR (CDCl$_3$,): 2.78 (s, 1H, OH), 3.85-3.93 (m, 1H, CH$_2$O), 4.00-4.09 (m, 1H, CH$_2$O), 5.14 (s, 2H, ArCH$_2$O), 5.40 (t, 1H, J=3.3 Hz, CH), 6.17 (d, 1H, J=6.4 Hz, NH), 7.35 (s, 5H, ArH), 7.49 (t, 2H, J=7.60 Hz, ArH), 7.62 (t, 1H, J=7.1 Hz, ArH), 8.99 (t, 2H, J=7.6 Hz, ArH).

$^{13}$C-NMR (CDCl$_3$,): 58.3, 64.6, 67.3, 128.1, 128.3, 128.6, 128.7, 129.0, 134.1, 136.0, 156.6, 196.6.

MS-ESI m/z (% rel. Int.): 300.1 ([MH]$^+$, 5), 256.1 (100).

HPLC: Method A, detection UV 254 nm, TTA 08010B RT=5.40 min, peak area 98.5%.

[ ]$^{22}_D$=−5.8 (c=1.00, MeOH).

Benzyl L-threo-1,3-dihydroxy-1-phenylpropan-2-ylcarbamate TTA 08012

To a stirred solution of benzyl (S)-3-hydroxy-1-oxo-1-phenylpropan-2-ylcarbamate TTA 08010B (1.40 g, 4.70 mmol) in 28 mL of anhydrous THF at −78° C. under nitrogen was added slowly dropwise 1 M DIBAL-H in hexane (18.8 mL, 18.80 mmol). The mixture was stirred 2 h at −78° C. then 1.5 h at RT. A solution of 2 M HCl (35 mL) was slowly added at −20° C. and the mixture was partitioned between ethyl acetate (750 mL) and acidic water. The organic phase was washed with water (2×20 mL), brine (2×20 mL) and dried over MgSO$_4$. After removing ethyl acetate by evaporation at 30-35° C., the crude product was purified by column chromatography on silica (CH$_2$Cl$_2$:MeOH=98:2 to 97:3) to give benzyl L-threo-1,3-dihydroxy-1-phenylpropan-2-ylcarbamate TTA 08012 as a white solid (1.10 g, 78% yield).

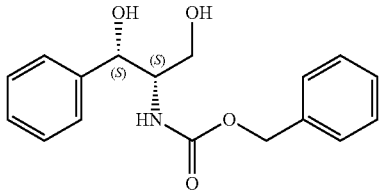

TTA 08012

MW: 301.34; Yield: 78%; White Solid; Mp (° C.): 102.5. $R_f$: 0.30 (CH$_2$Cl$_2$:MeOH=95/5).

$^1$H-NMR (CDCl$_3$,): 3.08 (t, 1H, J=5.0 Hz, OH), 3.59 (d, 1H, J=3.1 Hz, OH), 3.64-3.78 (m, 2H, CH$_2$O), 3.80-3.89 (m, 1H, CH), 4.95 (s, 2H, ArCH$_2$O), 5.57 (d, 1H, J=8.3 Hz, NH), 7.17-7.38 (m, 10H, ArH).

$^{13}$C-NMR (CDCl$_3$,): 57.5, 63.6, 66.9, 73.8, 126.0, 127.8, 127.9, 128.1, 128.5, 128.6, 136.2, 141.0, 156.9.

MS-ESI m/z (% rel. Int.): 302.0 ([MH]$^+$, 5); 132.0 (100).

HPLC: Method A, detection UV 254 nm, TTA 08012 RT=5.00 min, peak area 99.5%.

[ ]$^{22}_D$=+39.4 (c=1.00, MeOH).

Benzyl threo-1-hydroxy-3-morpholino-1-phenylpropan-2-ylcarbamate hydrochloride Compound 1

To a stirred solution of benzyl L-threo-1,3-dihydroxy-1-phenylpropan-2-ylcarbamate TTA 08012 (1.00 g, 3.30 mmol) in 13 mL of pyridine at −10° C. was added dropwise methanesulfonyl chloride (0.27 mL, 3.50 mmol). The mixture was stirred 6 h at 20° C. under nitrogen. Pyridine was removed by evaporation at 30-35° C. and the residue was partitioned between ethyl acetate (250 mL) and 0.1 N HCl (20 mL). The organic phase was washed with water (20 mL), brine (20 mL), dried over MgSO$_4$ and evaporated to give after drying L-threo-1-hydroxy-3-methanesulfonyl-1-phenylpropan-2-ylcarbamate TTA 08014 (1.25 g, 65% yield).

To a stirred solution of crude benzyl L-threo-1-hydroxy-3-methanesulfonyl-1-phenylpropan-2-ylcarbamate TTA 08014 (1.25 g, 3.30 mmol) in 6 mL of DMF at RT was added morpholine (1.2 mL, 13.20 mmol). The mixture was stirred 15 h at 50° C. under nitrogen. DMF was evaporated and the residue was partitioned between ethyl acetate (250 mL) and 1 N aqueous sodium bicarbonate (20 mL). The organic phase was washed with water (20 mL), brine (20 mL) and dried over MgSO$_4$. After evaporation the crude product was purified by column chromatography on silica (CH$_2$Cl$_2$:MeOH=98:2 to 97:3) to give benzyl L-threo-1-hydroxy-3-morpholino-1-phenylpropan-2-ylcarbamate as an oil (380 mg, 31% yield). The hydrochloride salt was obtained from 100 mg of the free base in diethylether at 0° C. using a solution 0.3 M HCl in diethylether. The precipitate was filtered and dry to give benzyl L-threo-1-hydroxy-3-morpholino-1-phenylpropan-2-ylcarbamate hydrochloride Compound 1 as a white solid (70 mg, 65% yield).

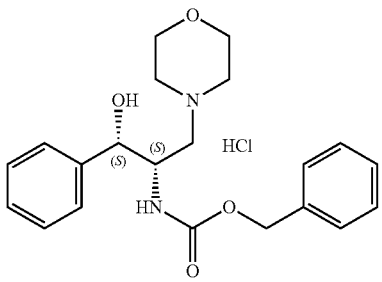

Compound 1

MW: 406.90; Yield: 20%; White Solid; Mp (° C.): 144.5. $R_f$: 0.40 (CH$_2$Cl$_2$:MeOH=95:5).

$^1$H-NMR (CD$_3$OD,): 3.14-3.77 (m, 6H, CH$_2$N), 3.70-4.07 (m, 4H, CH$_2$O), 4.30-4.33 (m, 1H, CH), 4.90-5.06 (m, 3H, CH, ArCH$_2$O), 7.20-7.43 (m, 10H, ArH).

$^{13}$C-NMR (CD$_3$OD,): 51.2, 51.8, 53.2, 59.3, 63.2, 66.3, 72.5, 125.8, 127.2, 127.3, 127.5, 127.8, 127.9.

MS-ESI m/z (% rel. Int.): 371.0 ([MH]$^+$, 100).

HPLC: Method A, detection UV 254 nm, Compound 1 RT=4.40 min, peak area 96.5%.

[ ]$^{22}_D$+13.9 (c=1.00, MeOH).

Preparation of threo-2-amino-3-morpholino-1-phenylpropan-1-ol dihydrochloride Compound 2

To a stirred solution of benzyl L-threo-1-hydroxy-3-morpholino-1-phenylpropan-2-ylcarbamate (Compound 1, 0.26 g, 0.70 mmol) in 20 mL of MeOH at RT was added Pd—C 10% (140 mg). The mixture was satured with hydrogen and stirred for 24 h at RT under hydrogen atmosphere (balloon). The catalyst Pd—C 10% was removed by filtration on celite and the solution was evaporated. The crude product was purified by column chromatography on silica (CH$_2$Cl$_2$:MeOH:NH$_4$OH=79:20:1 to 75:20:5) to give L-threo-2-amino-3-morpholino-1-phenylpropan-1-ol as an oil (100 mg, 60% yield). The hydrochloride salt was obtained from 83 mg of the free base in diethylether at 0° C. using 0.3 M HCl in diethylether. After precipitation in diethylether, filtration and drying L-threo-2-amino-3-morpholino-1-phenylpropan-1-ol dihydrochloride Compound 2 was obtained as a white solid (80 mg, 74% yield).

Compound 2

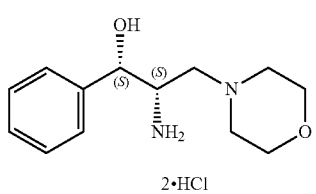

2·HCl

MW: 309.23; Yield: 44%; White Solid; Mp (° C.): 166.4-170.9.

R$_f$: 0.20 (CH$_2$Cl$_2$:MeOH=9:1).

$^1$H-NMR (CD$_3$OD,): 3.30-3.77 (m, 6H, CH$_2$N), 3.92-4.05 (m, 4H, CH$_2$O), 4.05-4.16 (m, 1H, CH), 4.85-4.98 (m, 1H, CH), 7.35-7.60 (m, 5H, ArH).

$^{13}$C-NMR (CD$_3$OD,): 53.1, 54.9, 58.5, 64.8, 72.6, 127.2, 128.0, 130.2, 140.3.

MS-ESI m/z (% rel. Int.): 237.0 ([MH]$^+$, 100).

HPLC: Method A, detection UV 254 nm, Compound 2 RT=0.90 min, peak area 98.0%.

[ ]$^{22}_D$+10.8 (c=1.00, MeOH), free base: [ ]$^{22}_D$=−6.1 (c=0.25, CHCl$_3$).

Preparation of benzyl L-threo-1-acetoxy-3-morpholino-1-phenylpropan-2-ylcarbamate hydrochloride Compound 3

Benzyl L-threo-1-acetoxy-3-morpholino-1-phenylpropan-2-ylcarbamate hydrochloride Compound 3

To a stirred solution of benzyl L-threo-1-hydroxy-3-morpholino-1-phenylpropan-2-ylcarbamate hydrochloride (Compound 1, 0.510 g, 1.25 mmol) in 30 mL of CHCl$_3$ at RT were added slowly triethylamine (700 mL, 5.00 mmol) and acetyl chloride (145 mL, 2.00 mmol). The mixture was stirred 10 h at RT under nitrogen and partitioned between a mixture of ice-water (20 mL) and CH$_2$Cl$_2$ (100 mL). The organic layer was washed with brine (20 mL) and dried over MgSO$_4$. After evaporation the crude product was purified by column chromatography on silica (CH$_2$Cl$_2$:MeOH=99.5:0.5 to 98:2) to give benzyl L-threo-1-acetoxy-3-morpholino-1-phenylpropan-2-ylcarbamate as an oil (0.420 g, 81% yield).

The hydrochloride salt was obtained from 45 mg of the free base in diethylether at 0° C. using a solution of 0.3 M HCl in diethylether. The precipitate was filtered and dry to give benzyl L-threo-1-acetoxy-3-morpholino-1-phenylpropan-2-ylcarbamate hydrochloride Compound 3 as a white solid (40 mg, 82% yield).

Compound 3

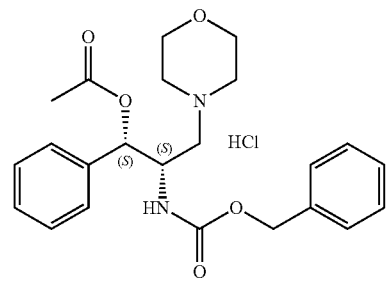

MW: 448.94; Yield: 66%; White Solid; Mp (° C.): 69.9.

R$_f$: 0.70 (CH$_2$Cl$_2$:MeOH=95:5).

$^1$H-NMR (CD$_3$OD,): 2.10 (s, 3H, CH$_3$), 3.14-3.44 (m, 4H, CH$_2$N), 3.70-4.00 (m, 4H, CH$_2$O), 4.51-4.53 (m, 1H, CH), 4.90-5.13 (m, 2H, ArCH$_2$O), 5.89 (d, 1H, CH), 7.28-7.48 (m, 10H, ArH).

$^{13}$C-NMR (CD$_3$OD,): 20.8, 52.0, 52.6, 59.7, 64.6, 68.0, 76.5, 127.7, 129.0, 129.2, 129.5, 129.8, 137.9, 158.7, 171.3.

MS-ESI m/z (% rel. Int.): 413.0 ([MH]$^+$, 100).

HPLC: Method A, detection UV 254 nm, Compound 3 RT=4.70 min, peak area 98.5%.

Preparation of DL-threo-2-(Decanamido)-1-(4-methoxyphenyl)-3-(pyrrolidin-1-yl)propyl decanoate Compound 10

2-Isocyano-1-(pyrrolidin-1-yl)ethanone BLE 04098

To stirred and cooled (0° C.) methyl isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from CH$_2$Cl$_2$:hexane to remove residual pyrrolidine. 2-Isocyano-1-(pyrrolidin-1-yl) ethanone BLE 04098 was obtained as a yellow solid (6.85 g, 98% yield) and used in the next step without purification.

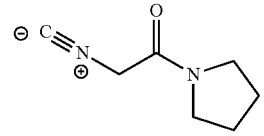

BLE 04098

MW: 138.17; Yield: 98%; yellow solid; Mp (° C.)=73.9.

$^1$H-NMR (CDCl$_3$,): 1.81-2.08 (m, 4H, 2×CH$_2$), 3.35-3.45 (m, 2H, —NCH$_2$), 3.50-3.60 (m, 2H, —NCH$_2$), 4.23 (s, 2H, CH$_2$CO).

Trans-(4,5-dihydro-5-(pyridin-3-yl)oxazol-4-yl)(pyrrolidin-1-yl)methanone BLE 04110B trans-(4,5-Dihydro-5-(4-methoxyphenyl)oxazol-4-yl) (pyrrolidin-1-yl)methanone SLA 07074

To a stirred and cooled (0° C.) solution of potassium hydroxide (0.37 g, 6.57 mmol) in methanol (30 mL) was added a mixture of 4-methoxy-benzaldehyde (0.88 mL, 7.23 mmol) and 2-isocyano-1-(pyrrolidin-1-yl)ethanone BLE 04098 (1.0 g, 6.57 mmol). The solution was stirred 4 h with continued cooling and then concentrated. The residue was partitioned between ethyl acetate and water. The organic layer was combined with additional ethyl acetate extracts, washed with aqueous sodium chloride and dried over MgSO$_4$. Concentration afforded a crude product as a glassy solid. Flash chromatography over silica (ethyl acetate) yielded to trans-(4,5-dihydro-5-(4-methoxyphenyl)oxazol-4-yl)(pyrrolidin-1-yl)methanone SLA 07074 as a pale yellow solid (1.2 g, 90.5%).

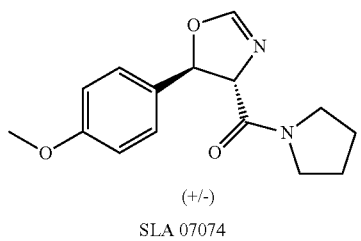 [SMILES: COc1ccc([C@H]2OC=N[C@@H]2C(=O)N2CCCC2)cc1]

(+/-)
SLA 07074

MW: 274.32; Yield: 90.5%; pale yellow solid; Mp (° C.): 91.2.

R$_f$: 0.30 (EtOAc).

$^1$H-NMR (CDCl$_3$,): 1.75-2.08 (m, 4H, 2×CH$_2$), 3.40-3.58 (m, 3H, CH$_2$N), 3.52 (s, 3H, CH$_3$O), 3.88-3.98 (m, 1H, CH$_2$N), 4.59 (dd, 1H, J=7.6 Hz, J=2.2 Hz, CH—N), 6.06 (d, 1H, J=7.6 Hz, CH—O), 6.90 (d, 2H, J=8.7 Hz, ArH), 7.01 (d, 1H, J=2.2 Hz, CH=N), 7.25 (d, 2H, J=8.7 Hz, ArH).

MS-ESI m/z (% rel. Int.): 275.1 ([MH]$^+$, 10), 247.1 (100).

HPLC: Method A, detection UV 280 nm, SLA 07074 RT=5.2 min, peak area 92%. DL-threo-2-Amino-3-hydroxy-3-(4-methoxyphenyl)-1-(pyrrolidin-1-yl)propan-1-one hydrochloride SLA 07078.

To a stirred solution of trans-(4,5-dihydro-5-(4-methoxyphenyl)oxazol-4-yl)(pyrrolidin-1-yl)methanone SLA 07074 (1.61 g, 5.93 mmol) in methanol (13 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-hydroxy-3-(4-methoxyphenyl)-1-(pyrrolidin-1-yl)propan-1-one hydrochloride SLA 07078 as a white solid (1.64 g, 93%).

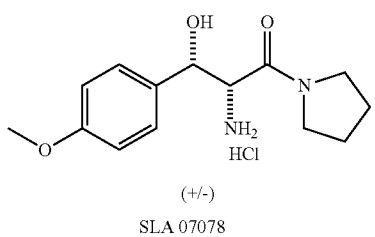 [SMILES: COc1ccc([C@H](O)[C@@H](N)C(=O)N2CCCC2)cc1 ; Cl]

(+/-)
SLA 07078

MW: 300.78; Yield: 93%; white Solid; Mp (° C.): 177.0.

$^1$H-NMR (CD$_3$OD,): 1.32-1.50 (m, 1H, CH$_2$), 1.50-1.88 (m, 3H, CH$_2$), 2.15-2.28 (m, 1H, CH$_2$N), 3.15-3.42 (m, 4H, 2×CH$_2$N), 3.79 (s, 3H, CH$_3$O), 4.06 (d, 1H, J=9.2 Hz, CH—N), 4.78 (d, 1H, J=9.2 Hz, CHO), 6.94 (d, 2H, J=8.5 Hz, ArH), 7.34 (d, 2H, J=8.5 Hz, ArH).

$^{13}$C-NMR (CD$_3$OD,): 24.8, 26.6, 47.2, 47.6, 55.9, 59.6, 73.9, 115.0 (2×C), 128.9 (2×C), 132.5, 161.7, 166.4.

DL-threo-2-Amino-1-(4-methoxyphenyl)-3-(pyrrolidin-1-yl)propan-1-ol Compound 9

To a stirred suspension of DL-threo-[5-(4-methoxy-phenyl)-4,5-dihydro-oxazol-4-yl]-pyrrolidin-1-yl-methanone SLA 07078 (1.61 g, 5.35 mmol) in tetrahydrofuran (200 mL) under nitrogen atmosphere was slowly added, in two portions, lithium aluminium hydride (1.22 g, 32.12 mmol) at 0° C. The mixture reaction was stirred at RT for 17 h, and then quenched by a slow, dropwise addition of water (50 mL). The white suspension was then concentrated to remove THF and taken back up in a mixture of 300 mL CH$_2$Cl$_2$ and 1N aqueous hydrochloric acid (50 mL). The aqueous layer was basified to pH=10-11 by a slow addition of 1N aqueous sodium hydroxyde. The organic layer was removed, combined with additional CH$_2$Cl$_2$ extracts (4×200 mL) and dried over MgSO$_4$, filtered and evaporated. The crude product was purified by column chromatography on silica (CH$_2$Cl$_2$:MeOH:NH$_3$=94:05:01). After evaporation and drying, DL-threo-2-amino-1-(4-methoxyphenyl)-3-(pyrrolidin-1-yl)propan-1-ol Compound 9 was obtained (0.62 g, 46%) as a pale yellow solid.

Compound 9

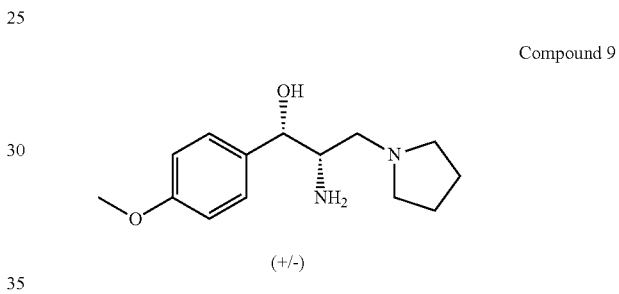

(+/-)

MW: 250.34; Yield: 46%; Pale Yellow Solid; Mp (° C.): 77.7.

R$_f$: 0.35 (CH$_2$Cl$_2$:MeOH:NH$_3$=94:05:01).

$^1$H-NMR (CDCl$_3$,): 1.65-1.87 (s, 4H, 2×CH$_2$), 2.40-2.90 (m, 9H, CH$_2$N, NH$_2$ &

OH), 3.11-3.17 (m, 1H, CH—N), 3.81 (s, 3H, CH$_3$O), 4.61 (d, 1H, J=3.8 Hz, CH—O), 7.89 (d, 2H, J=8.6 Hz, ArH), 7.26 (d, 2H, J=8.5 Hz, ArH).

$^{13}$C-NMR (CDCl$_3$,): 23.6 (2×C), 54.5, 54.7 (2×C), 55.3, 60.1, 75.9, 113.6, 127.4, 134.4, 158.8.

MS-ESI m/z (% rel. Int.): 251.1 ([MH]$^+$, 100).

DL-threo-2-(Decanamido)-1-(4-methoxyphenyl)-3-(pyrrolidin-1-yl)propyl decanoate Compound 10

To a stirred solution of DL-threo-2-amino-1-(4-methoxyphenyl)-3-pyrrolidin-1-yl-propan-1-ol Compound 9 (0.15 g, 0.60 mmol) in dichloromethane (10 mL) were added N-hydroxysuccinimide (0.07 g, 0.60 mmol), triethylamine (0.10 mL, 0.63 mmol) and decanoyl chloride (112 μL, 0.54 mmol) under nitrogen atmosphere. The mixture reaction was stirred at RT for 22 h and partitioned between methylene chloride and 1 N aqueous sodium hydroxide. The organic layer was dried over MgSO$_4$, filtered and evaporated. The crude product was purified by column chromatography on silica (CH$_2$Cl$_2$:MeOH=95:05). DL-threo-2-(Decanamido)-1-(4-methoxyphenyl)-3-(pyrrolidin-1-yl)propyl decanoate Compound 10 was obtained as a white oil (0.104 g, 31%).

Compound 10

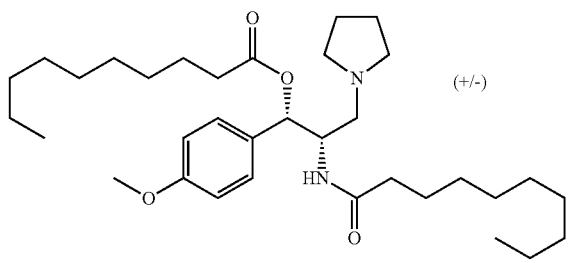

MW: 558.84; Yield: 40%; White Oil.
$R_f$: 0.35 (CH$_2$Cl$_2$:MeOH=95:05).
$^1$H-NMR (CDCl$_3$,): 0.88 (t, 6H, J=0.7 Hz, 2×CH$_3$), 1.26 (s, 14H, 7×CH$_2$), 1.57-1.59 (m, 4H, 2×CH$_2$), 1.80 (m, 4H, 2×CH$_2$), 2.10-2.50 (m, 5H, CH$_2$), 2.65-2.76 (m, 5H, CH$_2$), 3.79 (s, 3H, CH$_3$O), 4.54 (m, 1H, CH—N), 5.89 (d, 1H, J=6.2 Hz, CH—O), 6.16 (d broad, 1H, J=8.8 Hz, NH), 6.85 (d, 2H, J=8.7 Hz, ArH), 7.24 (d, 2H, J=8.7 Hz, ArH).
MS-ESI m/z (% rel. int.): 559.5 ([MH]$^+$, 100).
HPLC: Method A, detection UV 280 nm, Compound 10 RT=6.99 min, peak area 96.4%.

N-(DL-threo-1-Hydroxy-1-(4-methoxyphenyl)-3-(pyrrolidin-1-yl)propan-2-yl)palmitamide or DL-threo-4-MeO-P4 Compound 11

To a stirred solution of DL-threo-2-amino-1-(4-methoxyphenyl)-3-(pyrrolidin-1-yl)propan-1-ol Compound 9 (015 g, 0.60 mmol) in dichloromethane (10 mL) were successively added N-hydroxysuccinimide (0.07 g, 0.60 mmol), triethylamine (0.100 mL, 0.63 mmol) and palmitoyl chloride (0.15 g, 0.54 mmol) under nitrogen atmosphere. The mixture reaction was stirred at RT for 17 h and partitioned between methylene chloride and 1N aqueous sodium hydroxide. The organic layer was dried over MgSO$_4$, filtered and evaporated. The crude product was purified by column chromatography on silica (CH$_2$Cl$_2$:MeOH=95:05). N-(DL-threo-1-Hydroxy-1-(4-methoxyphenyl)-3-(pyrrolidin-1-yl)propan-2-yl)palmitamide Compound 11 was obtained as a white solid (0.117 g, 40%).

Compound 11

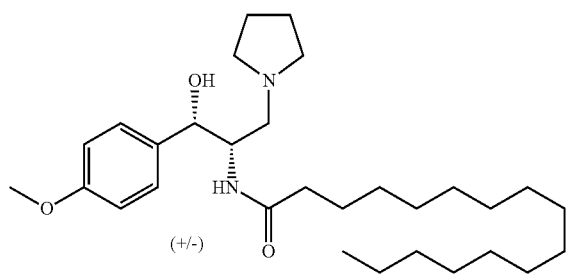

MW: 488.75; Yield: 40%; White Solid; Mp (° C.): 82.3.
$R_f$: 0.35 (CH$_2$Cl$_2$:MeOH=95:05).
$^1$H-NMR (CDCl$_3$: 0.88 (t, 3H, J=7.0 Hz, CH$_3$), 1.22-1.33 (m, 16H, 8×CH$_2$), 1.47-1.54 (m, 2H, CH$_2$), 1.81 (m, 4H, 2×CH$_2$), 2.09 (t, 2H, J=7.0 Hz, COCH$_2$), 2.60-2.80 (m, 4H, 2×CH$_2$), 2.84 (d, 2H, J=5.1 Hz, CH$_2$), 3.80 (s, 3H, CH$_3$O), 4.23 (m, 1H, CH—N), 5.00 (d, 1H, J=2.2 Hz, CH—O), 5.90 (d, 1H, J=7.4 Hz, NH), 6.87 (d, 2H, J=8.7 Hz, ArH), 7.24 (d, 2H, J=8.7 Hz, ArH).

$^{13}$C-NMR (CDCl$_3$,): 14.1, 22.7, 23.6, 25.6, 29.1, 29.3, 29.4, 29.5, 29.7, 29.7, 31.9, 36.8, 52.3, 55.2, 57.8, 75.4, 113.7 (2×C), 127.0 (2×C), 133.1, 158.9, 173.6.
MS-ESI m/z (rel. int.): 489.2 ([MH]$^+$, 100).
HP LC: Method A, detection UV 280 nm, Compound 11 RT=6.55 min, peak area 96.4%.

DL-threo-2-Amino-1-(2,3-dihydrobenzo[b][1,4]dioxin-6-yl)-3-(pyrrolidin-1-yl)propan-1-ol Compound 6 trans-(4,5-Dihydro-5-(2,3-dihydrobenzo[b][1,4]dioxin-6-yl)oxazol-4-yl)(pyrrolidin-1-yl)methanone BLE 04100

To a stirred and cooled (0° C.) solution of potassium hydroxide (0.43 mg, 7.60 mmol) in MeOH (6.5 mL) were added successively 1,4-benzodioxan-6-carboxaldehyde (1.31 g, 7.96 mmol) and 2-isocyano-1-(pyrrolidin-1-yl)ethanone BLE 04098 (1.0 g, 6.57 mmol). The solution was stirred 3 h at 0° C. and then concentrated. The residue was partitioned between EtOAc (100 mL) and water. The organic layer was combined with 2 additional EtOAc extracts (2×100 mL), washed with brine, dried over MgSO$_4$, filtered and evaporated. Concentration afford to a crude product which was purified by column chromatography on silica (EtOAc) to yield, after evaporation and drying, to trans-4,5-dihydro-5-(2,3-dihydrobenzo[b][1,4]dioxin-6-yl)oxazol-4-yl)(pyrrolidin-1-yl)methanone BLE 04100 as a colourless oil (1.76 g, 89% yield).

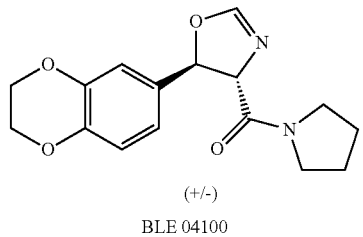 [SMILES: O=C([C@H]1N=CO[C@@H]1c1ccc2c(c1)OCCO2)N1CCCC1]

BLE 04100

MW: 440.49; Yield: 89%; colourless oil.
$^1$H-NMR (CDCl$_3$,): 1.75-2.10 (m, 4H, 2×CH$_2$), 3.40-3.59 (m, 6H, 3×CH$_2$N), 3.85-4.00 (m, 1H, CHN), 4.26 (s, 4H, CH$_2$O), 4.59 (dd, 1H, J=7.5 Hz, J=2.2 Hz, CH—N), 6.00 (d, 1H, J=7.5 Hz, CH—O), 6.75-6.90 (m, 3H, ArH), 7.00 (d, 1H, J=2.2 Hz, CH=N).

DL-threo-2-amino-3-(2,3-dihydrobenzo[b][1,4]dioxin-6-yl)-3-hydroxy-1-(pyrrolidin-1-yl)propan-1-one hydrochloride Compound 12

To a stirred solution of trans-4,5-dihydro-5-(2,3-dihydrobenzo[b][1,4]dioxin-6-yl)oxazol-4-yl)(pyrrolidin-1-yl) methanone BLE 04100 (1.74 g, 5.77 mmol) in methanol (15 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-(2,3-dihydrobenzo[b][1,4]dioxin-6-yl)-3-hydroxy-1-(pyrrolidin-1-yl)propan-1-one hydrochloride Compound 12 as a white solid (1.85 g, 95%).

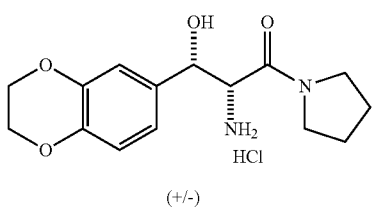

Compound 12

(+/-)

MW: 328.79; Yield: 95.0%; White Solid; Mp (° C.): 176.2.

$^{1}$H-NMR (CD$_{3}$OD,): 1.42-1.58 (m, 1H, CH$_{2}$), 1.58-1.70 (m, 1H, CH$_{2}$), 1.70-1.88 (m, 2H, CH$_{2}$), 3.20-3.45 (m, 4H, N—CH$_{2}$), 4.06 (d, 1H, J=9.1 Hz, CH—N), 4.25 (s, 2H, CH$_{2}$), 4.75 (d, 1H, J=9.2 Hz, CH—O), 4.89 (s, 2H, CH$_{2}$), 6.82-6.95 (m, 3H, ArH).

$^{13}$C-NMR (CD$_{3}$OD,): 24.9, 26.7, 47.3, 47.6, 59.5, 65.7, 73.6, 116.4, 118.3, 120.3, 133.7, 145.1, 145.6, 166.4.

DL-threo-2-Amino-1-(2,3-dihydrobenzo[b][1,4]dioxin-6-yl)-3-(pyrrolidin-1-yl)propan-1-ol Compound 6

To a stirred suspension of trans-(4,5-dihydro-5-(4-methoxyphenyl)oxazol-4-yl)(pyrrolidin-1-yl)methanone SLA 07080 (1.79 g, 5.44 mmol) in THF (220 mL) was slowly added at 0° C., in two portions, LiAlH4 (1.28 g, 33.7 mmol). The mixture was stirred at RT for 3.5 h and quenched by a slow addition of water at 0° C. (350 mL). The white suspension was concentrated to remove THF and taken back in a mixture of CH$_{2}$Cl$_{2}$ (300 mL) and 1 N aqueous HCl (50 mL). The aqueous layer was basified to pH=10-11 by slow addition of 1 N aqueous NaOH. The organic layer was removed; two more extracts were combined and dried over MgSO$_{4}$, filtered and evaporated. Concentration afforded to a crude product as a yellow oil. This material was purified by column chromatography on silica (CH$_{2}$Cl$_{2}$:MeOH:NH$_{4}$OH 20%=94:5:1) to led to DL-threo-2-amino-1-(2,3-dihydrobenzo[b][1,4]dioxin-6-yl)-3-(pyrrolidin-1-yl)propan-1-ol Compound 6 (0.705 g, 46.5% yield) as a near colorless gum.

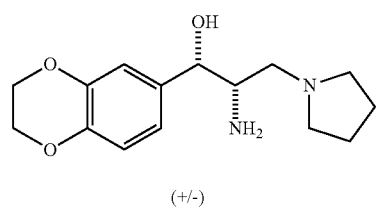

Compound 6

(+/-)

MW: 278.35; Yield: 46.5%; Colorless Gum.

R$_f$: 0.20 (CH$_{2}$Cl$_{2}$:MeOH:NH$_{4}$OH 20%=94:5:1).

$^{1}$H-NMR (CDCl$_{3}$,): 1.70-1.85 (m, 4H, 2×CH$_{2}$), 2.40-2.70 (m, 6H, 3×CH$_{2}$N—), 3.05-3.15 (m, 1H, CH—N), 4.25 (s, 4H, CH$_{2}$O), 4.55 (d, 1H, J=2.2 Hz, CH—O), 5.30 (s, 1H, —OH), 6.75-6.90 (m, 3H, ArH).

N-(DL-threo-1-(2,3-dihydrobenzo[b][1,4]dioxin-6-yl)-1-hydroxy-3-(pyrrolidin-1-yl)propan-2-yl)decanamide Compound 7

To a stirred solution of DL-threo-2-amino-1-(2,3-dihydrobenzo[b][1,4]dioxin-6-yl)-3-(pyrrolidin-1-yl)propan-1-ol BLE 04104 (0.186 g, 0.67 mmol) in 10 mL CH$_{2}$Cl$_{2}$ were added, in order, N-hydroxysuccinimide (0.081 g, 0.70 mmol) in 2 mL CH$_{2}$Cl$_{2}$, triethylamine (112 μL, 0.80 mmol) and decanoyl chloride (125 μL, 0.60 mmol). The mixture was stirred overnight at RT and then partitioned between CH$_{2}$Cl$_{2}$ and 1 N aqueous sodium hydroxide. The organic layer was dried over MgSO$_{4}$, filtered and evaporated and the residue obtained was purified by column chromatography on silica (CH$_{2}$Cl$_{2}$:MeOH=95:5). A white solid N-(DL-threo-1-(2,3-dihydrobenzo[b][1,4]dioxin-6-yl)-1-hydroxy-3-(pyrrolidin-1-yl)propan-2-yl)palmitamide Compound 7 was obtained (126 mg, 43.5% yield).

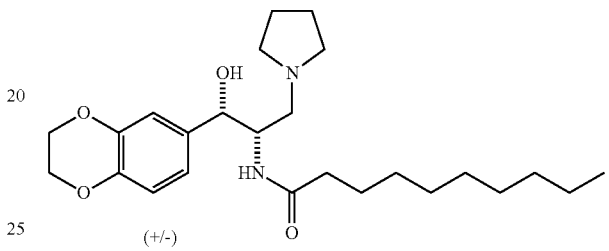

Compound 7

(+/-)

MW: 516.76; Yield: 43.5%; White Solid; Mp (° C.): 84.6.

R$_f$: 0.40 (MeOH:CH$_{2}$Cl$_{2}$=10:90).

$^{1}$H-NMR (CDCl$_{3}$,): 0.88 (t, 3H, J=6.7 Hz, CH$_{3}$), 1.12-1.39 (m, 12H), 1.40-1.60 (m, 2H, CH$_{2}$), 1.72-1.90 (m, 4H, 2×CH$_{2}$), 2.10 (t, 2H, J=6.7 Hz, CH$_{2}$), 2.55-2.90 (m, 6H), 4.13-4.30 (m, 1H, CH—N), 4.24 (s, 4H, CH$_{2}$N), 4.91 (d, 1H, J=3.3 Hz, CH—O), 5.90 (d, 1H, J=7.4 Hz, NH), 6.75-6.88 (m, 3H, ArH), OH not seen.

$^{13}$C-NMR (CDCl$_{3}$,): 14.1, 22.7, 23.6 (2×C), 25.6, 29.1, 29.3, 31.9, 36.8, 52.3, 55.1 (2×C), 57.7, 64.3 (2×C), 75.2, 77.2, 115.0, 117.0, 118.9, 134.4, 142.8, 143.4, 173.5, 174.8.

MS-ESI m/z (% rel. Int.): 433.1 ([MH]$^{+}$, 100).

HPLC: Method A, detection UV 280 nm, Compound 7, RT=5.2 min, peak area 96.2%.

N-(DL-threo-1-(2,3-Dihydrobenzo[b][1,4]dioxin-6-yl)-1-hydroxy-3-(pyrrolidin-1-yl)propan-2-yl)palmitamide Compound 8

To a stirred solution of DL-threo-2-amino-1-(2,3-dihydrobenzo[b][1,4]dioxin-6-yl)-3-(pyrrolidin-1-yl)propan-1-ol BLE 04104 (0.158 g, 0.57 mmol) in 10 mL CH$_{2}$Cl$_{2}$ were added, in order, N-hydroxysuccinimide (0.068 g, 0.59 mmol) in 2 ml CH$_{2}$Cl$_{2}$, triethylamine (95 μL, 0.68 mmol) and palmitoyl chloride (155 μL, 0.511 mmol) in 3 mL CH$_{2}$Cl$_{2}$. The mixture was stirred overnight at RT and then partitioned between CH$_{2}$Cl$_{2}$ and 1 N aqueous sodium hydroxyde. The organic layer was purified by column chromatography on silica using as eluent CH$_{2}$Cl$_{2}$:MeOH=95:5. A white solid N-(DL-threo-1-(2,3-dihydrobenzo[b][1,4]dioxin-6-yl)-1-hydroxy-3-(pyrrolidin-1-yl)propan-2-yl)palmitamide Compound 8 was obtained (148 mg, 50.4% yield).

Compound 8

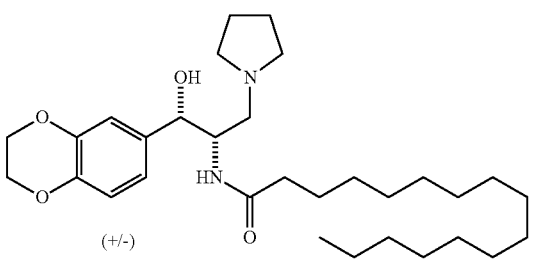

(+/-)

MW: 516.7; Yield: 50.4%; White Solid; Mp (° C.): 66.4. $R_f$: 0.50 (MeOH:CH$_2$Cl$_2$=10:90).
$^1$H-NMR (CDCl$_3$,): 0.88 (t, 3H, J=6.7 Hz, CH$_3$), 1.15-1.35 (m, 24H), 1.45-1.58 (m, 2H, CH$_2$), 1.75-1.90 (m, 4H, 2×CH$_2$), 2.10 (t, 2H, J=7.4 Hz, CH$_2$), 2.61 (s, 1H, OH), 2.52-2.72 (m, 4H), 2.72-2.92 (m, 2H), 4.15-4.22 (m, 1H, CH—N), 4.24 (s, 4H, CH$_2$N), 4.92 (d, 1H, J=3.3 Hz, CH—O), 6.08 (d, 1H, J=7.4 Hz, NH), 6.75-6.90 (m, 3H, ArH).
MS-ESI m/z (% rel. Int.): 517.2 ([MH]$^+$, 100).
HPLC: Method A, detection UV 280 nm, Compound 8 RT=6.60 min, peak area 97.2%.

Preparation of DL-threo-2-Amino-1-(pyridin-4-yl)-3-(pyrrolidin-1-yl)propan-1-ol Compound 46

Trans-(4,5-dihydro-5-(pyridin-3-yl)oxazol-4-yl)(pyrrolidin-1-yl)methanone BLE 04110B A general method D for oxazolines formation is illustrated by the preparation of BLE 04110B: To a stirred and cooled (0° C.) solution of potassium hydroxide (0.55 g, 9.80 mmol) in methanol (10 mL) were added a mixture of 3-pyridine carboxaldehyde (1.03 mL, 10.84 mmol) and 2-isocyano-1-(pyrrolidin-1-yl)ethanone BLE 04098 (1.50 g, 10.86 mmol). The solution was stirred 3 h at 0° C. and then concentrated. The residue was partitioned between ethyl acetate (100 mL) and water. The organic layer was combined with two additional ethyl acetate extracts (2×100 mL), washed with aqueous sodium chloride and dried over MgSO$_4$, filtered and evaporated. Concentration afforded a crude product which was purified by column chromatography on silica (CH$_2$Cl$_2$: MeOH=98:2) to yield to trans-(4,5-dihydro-5-(pyridin-3-yl)oxazol-4-yl)(pyrrolidin-1-yl)methanone BLE 04110B (0.95 g, 39%) as a pale yellow pale solid.

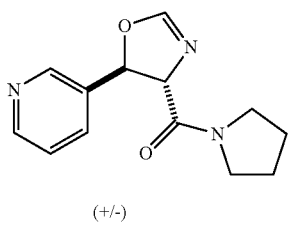

(+/-)

BLE 04110B

MW: 245.28; Yield: 39%; Yellow Pale Solid; Mp (° C.): 107.0.
$^1$H-NMR (CDCl$_3$,): 1.78-2.10 (m, 4H, 2×CH$_2$), 3.40-3.61 (m, 3H, CH$_2$N), 3.90-4.04 (m, 1H, CH$_2$N), 4.59 (dd, 1H, J=7.7 Hz, J=2.2 Hz, CH—N), 6.21 (d, 1H, J=7.7 Hz, CH—O), 7.04 (d, 1H, J=2.2 Hz, O—CH=N), 7.33 (m, 1H, ArH), 7.64 (m, 1H, ArH), 8.59 (d, 2H, J=2.8 Hz, ArH).
$^{13}$C-NMR (CDCl$_3$,): 24.2, 26.0, 46.4, 46.6, 75.7, 79.3, 123.7, 133.5, 135.3, 147.6, 149.9, 155.2, 166.2.

trans-(4,5-Dihydro-5-(pyridin-4-yl)oxazol-4-yl)(pyrrolidin-1-yl)methanone Compound 19

Compound 19 was prepared in accordance with method D using pyridine-4-carbaldehyde (1.88 mL, 19.76 mmol), KOH (1.01 g, 18.00 mmol) in methanol (18 mL) and 2-isocyano-1-(pyrrolidin-1-yl)ethanone BLE 04098 (2.73 g, 19.76 mmol). The residue was partitioned between ethyl acetate (200 mL) and water (150 mL). The organic layer was combined with additional ethyl acetate extracts (2×150 mL), washed with aqueous sodium chloride (2×150 mL) and dried over MgSO$_4$, filtered and evaporated. Trans-(4,5-dihydro-5-(pyridin-4-yl)oxazol-4-yl)(pyrrolidin-1-yl)methanone Compound 19 was obtained as a white solid (4.32 g, 98% yield).

Compound 19

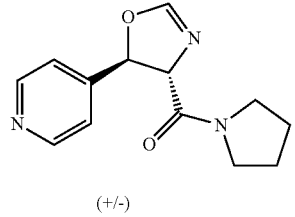

(+/-)

MW: 245.28; Yield: 98%; White Solid; Mp (° C.)=69.2. $R_f$: 0.65 (MeOH:CH$_2$Cl$_2$=10:90).
$^1$H-NMR (CDCl$_3$,): 1.78-2.06 (m, 4H, 2×CH$_2$), 3.44-3.60 (m, 3H, CH$_2$N), 3.90-4.01 (m, 1H, CH$_2$N), 4.52 (dd, 1H, J=7.9 Hz, J=2.2 Hz, CH—N), 6.19 (d, J=7.9 Hz, 1H, CH—O), 7.03 (d, 1H, J=2.2 Hz, N=CH—O), 7.24 (dd, 2H, J=4.5 Hz, J=1.5 Hz, ArH), 8.61 (dd, 2H, J=4.5 Hz, J=1.5 Hz, ArH).

A general method for the acidic hydrolysis of oxazolines (Method E) is illustrated in the preparation of Compound 20 which is a substituted propionic acid amide and is made from the oxazoline intermediate BLE 04110B which can be prepared in accordance with General Synthetic Scheme 1.

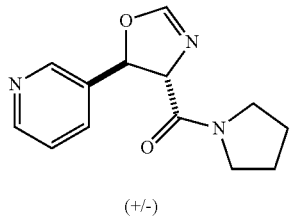

(+/-)

BLE 04110B

DL-threo-2-Amino-3-hydroxy-3-(pyridin-3-yl)-1-(pyrrolidin-1-yl)propan-1-one dihydrochloride Compound 20

To a solution of trans-(4,5-dihydro-5-(pyridin-3-yl)oxazol-4-yl)(pyrrolidin-1-yl)methanone BLE 04110B (0.932 g, 3.80 mmol) in methanol (10 mL) was added hydrochloric acid 37% (1.2 mL). After heating (50° C.) the mixture for 2.25 h the reaction mixture was concentrated and the crude product was coevaporated twice with ethyl acetate. After trituration with ethyl acetate, filtration and drying DL-threo-2-amino-3-hydroxy-3-(pyridin-3-yl)-1-(pyrrolidin-1-yl)propan-1-one dihydrochloride Compound 20 was obtained as a white solid (1.10 g, 94% yield).

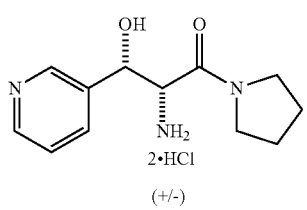

Compound 20

(+/-)

MW: 308.2; Yield: 94%; White Solid; Mp (° C.): 123.4.
$^1$H-NMR (CD$_3$OD,): 1.65-2.00 (m, 4H, 2×CH$_2$), 2.82-3.11 (m, 1H, —CH$_2$N), 3.30-3.57 (m, 2H, CH$_2$N), 3.57-3.77 (m, 1H, CH$_2$N), 4.54 (d, 1H, J=5.3 Hz, CH—N), 5.38 (d, 1H, J=5.3 Hz, CH—O), 8.15 (dd, 1H, J=7.6 Hz, J=5.0 Hz, ArH), 8.68 (d, 1H, J=7.6 Hz, ArH), 8.89 (d, 1H, J=7.6 Hz, ArH), 8.96 (s, 1H, ArH).
$^{13}$C-NMR (CD$_3$OD,): 24.9, 26.9, 47.7, 48.2, 58.1, 69.6, 128.7, 141.5, 141.6, 143.1, 146.5, 165.4.

DL-threo-2-Amino-3-hydroxy-3-(pyridin-4-yl)-1-(pyrrolidin-1-yl)propan-1-one dihydrochloride Compound 22

Compound 22 was prepared following method E with trans-(4,5-dihydro-5-(pyridin-4-yl)oxazol-4-yl)(pyrrolidin-1-yl)methanone Compound 19 (0.750 g, 3.07 mmol), hydrochloric acid 37% (1.0 mL) and methanol (10 mL). After 3.0 h at 50° C. and work-up DL-threo-2-amino-3-hydroxy-3-(pyridin-4-yl)-1-(pyrrolidin-1-yl)propan-1-one dihydrochloride Compound 22 was obtained as a white solid (0.935 g, 99%).

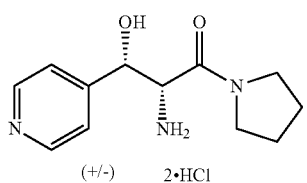

Compound 22

(+/-)   2·HCl

MW: 308.28; Yield: 99%; White Solid; Mp (° C.): 117.0.
$^1$H-NMR (CD$_3$OD,): 1.75-2.03 (m, 4H, 2×CH$_2$), 2.93-3.08 (m, 1H, CHN), 3.32-3.75 (m, 3H, 2×CH$_2$), 4.54 (d, 1H, J=5.9 Hz, CH—N), 5.40 (d, 1H, J=5.9 Hz, CH-0), 8.21 (d, 2H, J=5.8 Hz, ArH), 8.94 (d, 2H, J=5.8 Hz, ArH).
MS-ESI m/z (% rel. int.): 236.1 ([MH]$^+$, 17), 219 (25), 148 (100).
HPLC: Method A, detection UV 254 nm, Compound 22 RT=0.8 min, peak area 96.3%.

DL-threo-2-Amino-1-(pyridin-4-yl)-3-(pyrrolidin-1-yl)propan-1-ol Compound 46

To a stirred suspension of DL-threo-2-amino-3-hydroxy-3-(pyridin-4-yl)-1-(pyrrolidin-1-yl)propan-1-one dihydrochloride Compound 22 (0.86 g, 2.80 mmol) in tetrahydrofuran (108 mL) under nitrogen atmosphere was slowly added, in two portions, lithium aluminium hydride (0.64 g, 16.82 mmol) at 0° C. The mixture reaction was stirred at RT for 20 h and quenched by a slow, dropwise addition of 2 N aqueous sodium hydroxyde (8.4 mL, 6 eq). The yellow precipitate was filtered. The organic layer was washed by water (80 mL) and the organic layer was removed and combined with additional ethyl acetate extracts (4×200 mL) and dried over MgSO$_4$, filtered and evaporated. The crude product was purified by column chromatography on silica (CH$_2$Cl$_2$:MeOH:NH$_3$=94:05:01). After evaporation and drying DL-threo-2-amino-1-(pyridin-4-yl)-3-(pyrrolidin-1-yl)propan-1-ol Compound 46 was obtained (0.075 g, 12%) as a pale yellow solid.

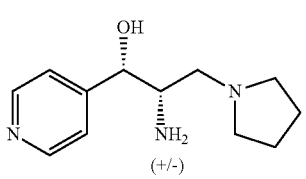

Compound 46

(+/-)

MW: 221.30; Yield: 12%; Pale Yellow Solid.
R$_f$: 0.35 (CH$_2$Cl$_2$:MeOH:NH$_3$=90:08:02).
$^1$H-NMR (CD$_3$OD,): 1.60-1.80 (m, 4H, 2×CH$_2$), 2.30-2.80 (m, 6H, 3×CH$_2$N), 3.14-3.19 (m, 1H, CH—NH$_2$), 4.68 (d, 1H, J=3.0 Hz, CH-0), 7.30 (d, 2H, J=6.0 Hz, ArH), 8.55 (d, 2H, J=6.0 Hz, ArH).
$^{13}$C-NMR (CD$_3$OD,): 23.5 (2×C), 54.1, 54.7 (2×C), 60.1, 74.5, 121.4 (2×C), 149.5 (2×C), 152.1.
MS-ESI m/z (rel. int.): 222.1 ([MH]$^+$, 100), 205.0 (80), 189.0 (45), 151.0 (70), 134.0 (42), 121.9 (100), 107.9 (40).

What is claimed is:

1. A compound having the formula

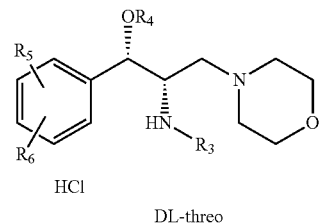

HCl

DL-threo where:
R$_3$ is CO—R$_7$ or CO—O—R$_7$;
R$_4$ is CO—R$_8$;
R$_5$ and R$_6$ are independently selected from H, alkyl of 1 to 6 carbons and alkoxy of 1 to 6 carbons;
R$_7$ is H, benzyl, alkyl of 1 to 20 carbons substituted with and NH$_2$ group, with a NHCOOalkyl or with an NH-COalkyl group where the alkyl group has 1 to 6 carbons, or R$_7$ is aryl, heteroaryl, aryl-alkyl or heteroaryl-alkyl where the alkyl moiety is branched or unbranched and has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons;
R$_8$ is alkyl of 1 to 6 carbons;
or any other pharmaceutically acceptable salt of said compound.

2. A compound in accordance with claim 1 having the formula

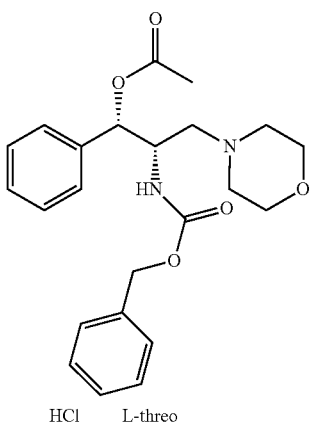 [SMILES: CC(=O)O[C@@H](c1ccccc1)[C@H](CN1CCOCC1)NC(=O)OCc1ccccc1 ; Cl]

HCl   L-threo or any other pharmaceutically acceptable salt of said compound.

3. A method of treating pain in a mammal, the method comprising the step of administering to said mammal in need of such treatment a compound in accordance with claim 1 or a pharmaceutically acceptable salt thereof.

4. A method of treating pain in a mammal, the method comprising the step of administering to said mammal in need of such treatment a compound in accordance with claim 2 or a pharmaceutically acceptable salt thereof.

5. The method of claim 3, wherein said pain is chronic pain.

6. The method of claim 4, wherein said pain is chronic pain.

7. A pharmaceutical composition comprising a compound in accordance with claim 1, or a pharmaceutically acceptable salt thereof, and a pharmaceutically acceptable excipient.

8. A pharmaceutical composition comprising a compound in accordance with claim 2, or a pharmaceutically acceptable salt thereof, and a pharmaceutically acceptable excipient.

\* \* \* \* \*